United States Patent
Elomari

(10) Patent No.: US 6,632,417 B2
(45) Date of Patent: *Oct. 14, 2003

(54) PROCESS FOR PREPARING ZEOLITES

(75) Inventor: Saleh Elomari, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/905,459

(22) Filed: Jul. 13, 2001

(65) Prior Publication Data

US 2002/0085976 A1 Jul. 4, 2002

Related U.S. Application Data

(63) Continuation-in-part of application No. 09/520,640, filed on Mar. 7, 2000, now Pat. No. 6,475,463, and a continuation-in-part of application No. 09/836,923, filed on Apr. 17, 2001, which is a continuation-in-part of application No. 09/584,187, filed on May 31, 2000, now abandoned.

(51) Int. Cl.[7] .................... C01B 39/04; C01B 39/40; C01B 39/42

(52) U.S. Cl. ................ 423/706; 423/DIG. 22; 423/DIG. 33

(58) Field of Search ................. 423/705, 706, 423/DIG. 22, DIG. 33

(56) References Cited

U.S. PATENT DOCUMENTS

| | | |
|---|---|---|
| 3,702,886 A | 11/1972 | Argauer et al. |
| 3,832,449 A | 8/1974 | Rosinski et al. |
| 4,287,166 A | 9/1981 | Dwyer et al. |
| 4,397,827 A | 8/1983 | Chu |
| 4,568,654 A | 2/1986 | Valyocsik |
| 4,585,746 A * | 4/1986 | Valyocsik |
| 5,554,356 A * | 9/1996 | Saxton et al. |
| 6,080,382 A | 6/2000 | Lee et al. |

OTHER PUBLICATIONS

U.S. patent application Ser. No. 09/520,640, Elomari et al.
U.S. patent application Ser. No. 09/584,187, 09/836,923, 09/905,461, Elomari.
Szostak, Handbook of Molecular Sieves, Van Nostrand Reinhold, 1992, pp. 518–527, 547–549, 551–553, 554–555, 532–533.

* cited by examiner

Primary Examiner—David Sample
(74) Attorney, Agent, or Firm—Richard J. Sheridan

(57) ABSTRACT

The present invention relates to a process for preparing zeolites using quaternary ammonium cations having the following formula as structure directing agents:

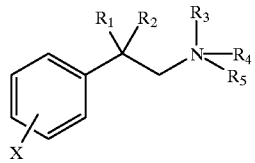

Formula (I)

wherein:

X is —H, methyl, —F, —Cl, —F and —Cl, or methoxy;

$R_1$ and $R_2$ are each methyl or ethyl; $R_1$ and $R_2$ together are —$(CH_2)_x$— where x is 2, 3, 4, or 5; or $R_1$ and $R_2$ together are methylated or dimethylated —$(CH_2)_y$— where y is 3, 4, or 5; and $R_3$, $R_4$ and $R_5$ are each methyl or ethyl, or one of $R_3$, $R_4$ or $R_5$ is methyl and the other two together are —$(CH_2)_z$— where z is 4, 5, 6 or 7;.

65 Claims, No Drawings

PROCESS FOR PREPARING ZEOLITES

CROSS REFERENCE TO RELATED APPLICATION

This application is a continuation-in-part of application Ser. No. 09/520,640, now U.S. Pat. No. 6,475,463, filed Mar. 7, 2000 and application Ser. No. 09/836,923, now U.S. Publication No. 2002 0104780 filed Apr. 17, 2001 which is a continuation-in-part of Ser. No. 09/584,187, filed May 31, 2000 now abandoned.

BACKGROUND OF THE INVENTION

Field of the Invention

The present invention relates to a process for preparing zeolites using quaternary ammonium cations as a structure directing agent (SDA).

SUMMARY OF THE INVENTION

In accordance with the present invention, there is provided a process for preparing a zeolite which comprises:

(a) preparing an aqueous solution from (1) sources of an alkali metal oxide, alkaline earth metal oxide or mixtures thereof, (2) sources of an oxide selected from oxides of silicon, germanium or mixtures thereof, (3) sources of an oxide selected from the oxides of aluminum, boron, iron, gallium, indium, titanium, vanadium or mixtures thereof, and (4) at least one quaternary ammonium cation capable of forming the zeolite having the formula

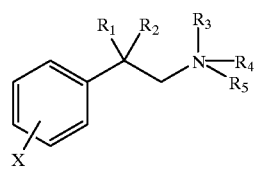

Formula (I)

wherein:

X is —H, methyl, —F, —Cl, —F and —Cl, or methoxy;

$R_1$ and $R_2$ are each methyl or ethyl; $R_1$ and $R_2$ together are —$(CH_2)_x$— where x is 2, 3, 4, or 5; or $R_1$ and $R_2$ together are methylated or dimethylated —$(CH_2)_y$— where y is 3, 4, or 5; and $R_3$, $R_4$ and $R_5$ are each methyl or ethyl, or one of $R_3$, $R_4$ or $R_5$ is methyl and the other two together are —$(CH_2)_z$— where z is 4, 5, 6 or 7;

(b) maintaining the aqueous solution under conditions sufficient to form crystals of the zeolite; and (c) recovering the crystals of the zeolite.

The present invention also provides this process further comprising replacing alkali and/or alkaline earth metal cations of the recovered zeolite, at least in part, by ion exchange with a cation or mixture of cations selected from the group consisting of hydrogen and hydrogen precursors, rare earth metals, and metals from Groups IIA, IIIA, IVA, IB, IIB, IIIB, IVB, VIB, and VIII of the Periodic Table of Elements.

The present invention also provides a zeolite composition, as-synthesized and in the anhydrous state, whose general composition, in terms of mole ratios, is as follows:

$YO_2/W_cO_d \geq 20$ $Q/YO_2$ 0.02–0.10

$M_{2/n}/YO_2$ 0.01–0.10 wherein Y is silicon, germanium or a mixture thereof; W is aluminum, boron, gallium, indium, iron, titanium, vanadium or mixtures thereof; c is 1 or 2; d is 2 when c is 1 (i.e., W is tetravalent) or d is 3 or 5 when c is 2 (i.e., d is 3 when W is trivalent or 5 when W is pentavalent); Q is at least one quaternary ammonium cation capable of forming the zeolite and having formula (I) above; M is an alkali metal cation, alkaline earth metal cation or mixtures thereof; and n is the valence of M (i.e., 1 or 2).

DETAILED DESCRIPTION OF PREFERRED EMBODIMENTS

The present invention comprises:

(a) preparing an aqueous solution from sources of oxides capable of forming a zeolite and at least one quaternary ammonium cation capable of forming the zeolite and having formula (I) above;

(b) maintaining the aqueous solution under conditions sufficient to form crystals of the zeolite; and (c) recovering the crystals of the zeolite.

The process of the present invention comprises forming a reaction mixture from sources of alkali and/or alkaline earth metal (M) cations with valences n (i.e., 1 or 2); sources of an oxide of aluminum, boron, iron, gallium, indium, titanium, vanadium or mixtures thereof (W); sources of an oxide of silicon, germanium or mixtures thereof (Y); at least one quaternary ammonium cation of this invention (Q); and water, said reaction mixture having a composition in terms of mole ratios within the following ranges:

| Reactants | General | Preferred |
| --- | --- | --- |
| $YO_2/W_aO_b$ | 20–∞ | 25–90 |
| $OH^-/YO_2$ | 0.10–0.50 | 0.15–0.30 |
| $Q/YO_2$ | 0.05–0.50 | 0.10–0.30 |
| $M_{2/n}/YO_2$ | 0.02–0.40 | 0.01–0.30 |
| $H_2O/YO_2$ | 10–100 | 25–50 | where Y, W, Q, M and n are as defined above, and a is 1 or 2, and b is 2 when a is 1 (i.e., W is tetravalent) and b is 3 when a is 2 (i.e., W is trivalent).

Typical sources of aluminum oxide for the reaction mixture include aluminates, alumina, hydrated aluminum hydroxides, and aluminum compounds such as $AlCl_3$ and $Al_2(SO_4)_3$. Typical sources of silicon oxide include silica hydrogel, silicic acid, colloidal silica, tetraalkyl orthosilicates, silica hydroxides, and fumed silicas. Gallium, iron, boron, indium, titanium, vanadium and germanium can be added in forms corresponding to their aluminum and silicon counterparts. Trivalent elements stabilized on silica colloids are also useful reagents.

The quaternary ammonium cations useful in the practice of this invention are those which are capable of forming a zeolite. The quaternary ammonium cations of this invention are represented by the following formula:

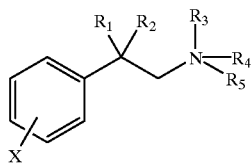

Formula (I)

wherein:
X is —H, methyl, —F, —Cl, —F and —Cl, or methoxy;
$R_1$ and $R_2$ are each methyl or ethyl; $R_1$ and $R_2$ together are —$(CH_2)_x$— where x is 2, 3, 4, or 5; or $R_1$ and $R_2$ together are methylated or dimethylated —$(CH_2)_y$— where y is 3, 4, or 5; and $R_3$, $R_4$ and $R_5$ are each methyl or ethyl, or one of $R_3$, $R_4$ or $R_5$ is methyl and the other two together are —$(CH_2)_z$— where z is 4, 5, 6 or 7.

In preparing the zeolites in accordance with the present invention, the reactants and the SDA are dissolved in water and the resulting reaction mixture is maintained at an elevated temperature until crystals are formed. The hydrothermal crystallization is usually conducted under autogenous pressure, at a temperature between 100° C. and 200° C., preferably between 135° C. and 160° C. The crystallization period is typically greater than 1 day and preferably from about 3 days to about 20 days.

The hydrothermal crystallization is usually conducted under pressure and usually in an autoclave so that the reaction mixture is subject to autogenous pressure. The reaction mixture should be stirred during crystallization.

Once the crystals have formed, the solid product is separated from the reaction mixture by standard mechanical separation techniques, such as filtration. The crystals are water-washed and then dried, e.g., at 90° C. to 150° C. for from 8 to 24 hours, to obtain the as-synthesized zeolite crystals. The drying step can be performed at atmospheric or subatmospheric pressures.

During the hydrothermal crystallization step, the crystals can be allowed to nucleate spontaneously from the reaction mixture. The reaction mixture can also be seeded with crystals of the desired zeolite both to direct, and accelerate the crystallization, as well as to minimize the formation of any undesired crystalline phases. When seed crystals are used, typically about 0.5% to about 5.0% by weight (based on the weight of silica used in the reaction mixture) of the seed crystals are added.

Due to the unpredictability of the factors which control nucleation and crystallization in the art of crystalline oxide synthesis, not every combination of reagents, reactant ratios, and reaction conditions will result in crystalline products. Selecting crystallization conditions which are effective for producing crystals may require routine modifications to the reaction mixture or to the reaction conditions, such as temperature, and/or crystallization time. Making these modifications are well within the capabilities of one skilled in the art.

The zeolite products made by the process of this invention have an as-synthesized composition comprising, in terms of mole ratios in the anhydrous state, the following:

$YO_2/W_cO_d \geq 20$
$Q/YO_2$ 0.02–0.10
$M_{2/n}/YO_2$ 0.01–0.10 wherein Y, W, c, d, Q, M and n are as defined above. Preferably, Y is silicon, W is aluminum, and M is sodium.

The zeolite products made in accordance with this invention were identified by their X-ray diffraction (XRD) pattern. The X-ray powder diffraction patterns were determined by standard techniques. The radiation was the K-alpha/doublet of copper. In the X-ray data shown below, the peak heights I and the positions, as a function of 2 theta where theta is the Bragg angle, were read from the relative intensities, $100 \times I/I_0$ where $I_0$ is the intensity of the strongest line or peak, and d, the interplanar spacing in Angstroms corresponding to the recorded lines, can be calculated.

The SDA's of this invention can be used to prepare a variety of zeolites, including ZSM-5, ZSM-12, ZSM-39, ZSM-48, ZSM-51, SSZ-48, SSZ-53, SSZ55, and SSZ-59. Table A below shows the zeolites that have been made using the quaternary ammonium cations of this invention, as well as the particular cations that can be used to make each zeolite. It should be noted that in Table A, "Me" represents a methyl group and the positive charge on the nitrogen atom is not shown.

TABLE A

| SDA No. | SDA | Zeolitic Products |
|---|---|---|
| 1 | N,N,N-Trimethyl(2-methyl-2-*m*-tolylpropyl)ammonium cation | ZSM-39 |
| 2 | N,N,N-Trimethyl(2-ethyl-2-*m*-tolylbutyl)ammonium cation | ZSM-39, ZSM-51 |
| 3 | N,N,N-Trimethyl(2-methyl-2-*o*-tolylpropyl)ammonium cation | ZSM-39, ZSM-51 |
| 4 | N,N,N-Trimethyl(2-ethyl-2-*o*-tolylbutyl)ammonium cation | ZSM-39 |
| 5 | N,N,N-Trimethyl(2-methyl-2-p-tolylpropyl)ammonium cation | ZSM-39, ZSM-51 |

TABLE A-continued

| SDA No. | SDA | Zeolitic Products |
|---|---|---|
| 6 | N,N,N-Trimethyl(2-ethyl-2-*p*-tolylbutyl)ammonium cation | ZSM-48, ZSM-39 |
| 7 | N,N,N-Trimethyl((*p*-tolylcyclopentyl)methyl)ammonium cation | ZSM-39 |
| 8 | N,N,N-Trimethyl(2-methyl-2-phenylpropyl)ammonium cation | ZSM-39, ZSM-5 |
| 9 | N,N,N-Trimethyl(2-methyl-2-phenylbutyl)ammonium cation | ZSM-39, ZSM-5 |
| 10 | N,N,N-Trimethyl(2-methyl-2-propylpenyl)ammonium cation | ZSM-39, ZSM-5 |
| 11 | N,N,N-Trimethyl((phenlcyclopropyl)methyl)ammonium cation | SSZ-48 |
| 12 | Trimethyl(phenylcyclobutyl)methyl)ammonium cation | SSZ-48, SSZ-55 |
| 13 | Trimethyl(phenylcyclopentyl)methyl)ammonium cation | SSZ-53 |
| 14 | Trimethyl(phenylcyclohexyl)methyl)ammonium cation | SSZ-53 |
| 15 | Trimethyl[(1-(2-fluorophenyl)cyclopentyl)methyl]ammonium cation | SSZ-53 |
| 16 | Trimethyl[(1-(3-fluorophenyl)cyclopentyl)methyl]ammonium cation | SSZ-53, SSZ-55 |
| 17 | Trimethyl[(1-(4-fluorophenyl)cyclopentyl)methyl]ammonium cation | SSZ-53 |
| 18 | Trimethyl[(1-(4-chlorophenyl)cyclohexyl)methyl]ammonium cation | SSZ-53 |
| 19 | Trimethyl[(1-(2-chloro-6-fluorophenyl)cyclopentyl)methyl]ammonium cation | SSZ-53 |

TABLE A-continued

| SDA No. | SDA | Zeolitic Products |
|---|---|---|
| 20 | Trimethyl[(1-(4-chloro-2-fluorophenyl)cyclohexyl)methyl]ammonium cation | SSZ-53 |
| 21 | Trimethyl[(1-(4-chlorophenyl)cyclopropyl)methyl]ammonium cation | SSZ-48 |
| 22 | Trimethyl[(2-methyl-1-phenylcyclopentyl)methyl]ammonium cation | SSZ-53 |
| 23 | Methyl[(1-(4-chlorophenyl)cyclopentyl)methyl]pyrrolidinium cation | SSZ-53 |
| 24 | N-methyl[(1-(4-chlorophenyl)cyclopentyl)methyl]piperidinium cation | SSZ-59 |
| 25 | N-methyl-N-[(1-(4-chlorophenyl)cyclopentyl)methyl]hexa-methyleneiminium cation | SSZ-59 |
| 26 | N-methyl-N-[(1-(4-chlorophenyl)cyclopentyl)methyl]hepta-methyleneiminium cation | SSZ-59 |
| 27 | Trimethyl[(1-(4-methoxyphenyl)cyclohexyl)methyl]ammonium cation | ZSM-12, ZSM-5, ZSM-39 |
| 28 | Trimethyl[(1-(4-methylphenyl)cyclohexyl)methyl] ammonium cation | ZSM-39 |
| 29 | N-methyl-N-[(1-phenylcyclopentyl)methyl]piperidinium cation | SSZ-59 |
| 30 | N-methyl-N-[(1-phenylcyclopentyl)methyl]hepta-methyleneiminium cation | SSZ-59 |

TABLE A-continued

| SDA No. | SDA | Zeolitic Products |
|---|---|---|
| 31 | 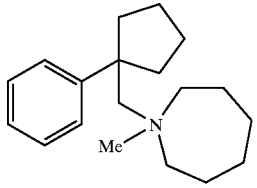<br>N-methyl-N-[(1-phenylcyclopentyl)methyl]hexa-methyleneiminium cation | SSZ-59 |
| 32 | 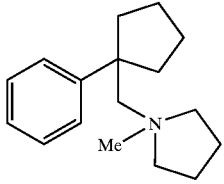<br>N-methyl-N-[(phenylcyclopentyl)methylpyrrolidinium cation | SSZ-53 |
| 33 | 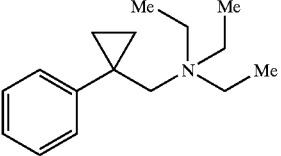<br>Triethyl[(phenylcyclopropyl)methyl]ammonium cation | SSZ-48 |

ZSM-5

ZSM-5 is a well known zeolite. It is disclosed in Szostak, "Handbook of Molecular Sieves", Van Nostrand Reinhold, 1992 and in U.S. Pat. No. 3,702,886 (issued Nov. 14, 1972 to Argauer et al.), both of which are incorporated herein by reference in their entirety.

ZSM-12

ZSM-12 is another well known zeolite. It is disclosed in Szostak, "Handbook of Molecular Sieves", Van Nostrand Reinhold, 1992 and in U.S. Pat. No. 3,832,449 (issued Aug. 27, 1974 to Rosinski et al.), both of which are incorporated herein by reference in their entirety.

ZSM-39

ZSM-39 is also a known zeolite. It is disclosed in Szostak, "Handbook of Molecular Sieves", Van Nostrand Reinhold, 1992 and in U.S. Pat. No. 4,287,166 (issued Sep. 1, 1981 to Dweyer et al.), both of which are incorporated herein by reference in their entirety.

ZSM-48

ZSM-48 is also a known zeolite. It is disclosed in Szostak, "Handbook of Molecular Sieves", Van Nostrand Reinhold, 1992 and in U.S. Pat. No. 4,397,827 (issued Aug. 9, 1983 to Chu), both of which are incorporated herein by reference in their entirety.

ZSM-51

ZSM-51 is also a known zeolite. It is disclosed in Szostak, "Handbook of Molecular Sieves", Van Nostrand Reinhold, 1992 and in U.S. Pat. No. 4,568,654 (issued Feb. 4, 1986 to Valyocsik), both of which are incorporated herein by reference in their entirety.

SSZ-48

Zeolite SSZ-48 is a known zeolite. It is disclosed in U.S. Pat. No. 6,080,382 (issued Jun. 27, 2000 to Lee et al.) which is incorporated herein by reference in its entirety.

SSZ-53

SSZ-53 is disclosed in copending U.S. patent application Ser. No. 09/836,923, filed Apr. 17, 2001, which is a continuation-in-part of Ser. No. 09/584,187, filed May 31, 2000. Both applications are incorporated herein by reference in their entirety.

SSZ-53 is prepared from a reaction mixture having the composition shown in Table 1 below.

TABLE 1

| SSZ-53 Reaction Mixtures | | |
|---|---|---|
| | Typical | Preferred |
| $YO_2/W_aO_b$ | 20–150 | 35–60 |
| $OH^-/YO_2$ | 0.1–0.50 | 0.2–0.3 |
| $Q/YO_2$ | 0.05–0.5 | 0.1–0.2 |
| $M_{2/n}/YO_2$ | 0.02–0.4 | 0.1–0.25 |
| $H_2O/YO_2$ | 25–80 | 30–45 | where Y is silicon, germanium or a mixture thereof; W is aluminum, gallium, iron, boron, titanium, indium, vanadium or mixtures thereof; M is an alkali metal cation, alkaline earth metal cation or mixtures thereof; n is the valence of M (i.e., 1 or 2); a is 1 or 2, and b is 2 when a is 1 (i.e., W is tetravalent) and b is 3 when a is 2 (i.e., W is trivalent) and Q is the SDA.

SSZ-53, as prepared, has a mole ratio of an oxide selected from silicon oxide, germanium oxide and mixtures thereof to an oxide selected from aluminum oxide, gallium oxide, iron oxide, boron oxide, titanium oxide, indium oxide, vanadium oxide and mixtures thereof greater than about 20; and has the X-ray diffraction lines of Table 3 below. SSZ-53 further has a composition, as-synthesized and in the anhydrous state, in terms of mole ratios, shown in Table 2 below.

TABLE 2

| As-Synthesized SSZ-53 | |
|---|---|
| $YO_2/W_cO_d$ | 20–150 |
| $M_{2/n}/YO_2$ | 0.01–0.03 |
| $Q/YO_2$ | 0.02–0.05 | where Y, W, M and n are as defined above, c is 1 or 2; d is 2 when c is 1 (i.e., W is tetravalent) or d is 3 or 5 when c is 2 (i.e., d is 3 when W is trivalent or 5 when W is pentavalent) and Q is the SDA.

SSZ-53 zeolites, as-synthesized, have a crystalline structure whose X-ray powder diffraction pattern exhibit the characteristic lines shown in Table 3 and is thereby distinguished from other zeolites.

TABLE 3

As-Synthesized SSZ-53

| 2 Theta[a] | d | Relative Intensity[b] |
|---|---|---|
| 6.65 | 13.3 | VS |
| 8.3 | 10.6 | S |
| 17.75 | 4.99 | S |
| 19.8 | 4.48 | S |
| 21.2 | 4.19 | VS |
| 23.05 | 3.85 | W |
| 25.3 | 3.52 | M |
| 35.8 | 2.51 | M |

[a]±0.15
[b]The X-ray patterns provided are based on a relative intensity scale in which the strongest line in the X-ray pattern is assigned a value of 100: W (weak) is less than 20; M (medium) is between 20 and 40; S (strong) is between 40 and 60; VS (very strong) is greater than 60.

After calcination, the SSZ-53 zeolites have a crystalline structure whose X-ray powder diffraction pattern include the characteristic lines shown in Table 4.

TABLE 4

Calcined SSZ-53

| 2 Theta[a] | d | Relative Intensity |
|---|---|---|
| 6.65 | 13.3 | VS |
| 8.3 | 10.6 | S |
| 17.75 | 4.99 | M |
| 19.7 | 4.50 | M |
| 21.0 | 4.23 | M |
| 23.0 | 3.86 | W |
| 25.15 | 3.544 | W |
| 35.6 | 2.52 | W |

[a]±0.15

In addition to the peaks in Tables 3 and 4, there are peaks at 2 theta 22.0 and 21.6. These peaks may be partially overlapped with the peak at 2 theta 21.0, or appear as shoulders. Thus, the peaks at 2 theta 22.0 and 21.6 may be difficult to locate, especially if the SSZ-53 has a small crystal size.

SSZ-55

SSZ-55 is disclosed in copending U.S. patent application Ser. No. 09/520,640, filed Mar. 7, 2000 which is incorporated herein by reference in its entirety. SSZ-55 is a zeolite having a composition, as synthesized and in the anhydrous state, in terms of mole ratios as follows:

As-synthesized SSZ-55

$YO_2/W_cO_d$ 20–150
$M_{2/n}/YO_2$ 0.01–0.03
$Q/YO_2$ 0.02–0.05 where Y, W, c, d, M and n are as defined above and Q is an SDA. SSZ-55 can be prepared from reaction mixtures shown in the table below.

SSZ-55 Reaction Mixtures

| | Typical | Preferred |
|---|---|---|
| $YO_2/W_aO_b$ | 20–150 | 35–60 |
| OH—/$YO_2$ | 0.1–0.50 | 0.2–0.3 |
| $Q/YO_2$ | 0.05–0.5 | 0.1–0.2 |
| $M_{2/n}/YO_2$ | 0.02–0.4 | 0.1–0.25 |
| $H_2O/YO_2$ | 25–80 | 30–45 | where Y, W, a, b, M and n are as defined above and Q is the SDA.

SSZ-55 zeolites, as-synthesized, have a crystalline structure whose X-ray powder diffraction pattern exhibit the characteristic lines shown in Table 5 and is thereby distinguished from other zeolites.

TABLE 5

As-Synthesized SSZ-55

| 2 Theta[a] | D | Relative Intensity |
|---|---|---|
| 7.94 | 11.13 | S |
| 15.98 | 5.54 | M |
| 16.60 | 5.33 | 5 |
| 19.24 | 4.61 | M |
| 20.97 | 4.23 | VS |
| 21.93 | 4.05 | M |
| 22.48 | 3.95 | VS |
| 23.68 | 3.75 | M |
| 27.54 | 3.24 | M |
| 35.08 | 2.56 | W |

[a]±0.2.

After calcination, the SSZ-55 zeolites have a crystalline structure whose X-ray powder diffraction pattern include the characteristic lines shown in Table 6.

TABLE 6

Calcined SSZ-55

| 2 Theta[a] | D | Relative Intensity |
|---|---|---|
| 7.94 | 11.13 | VS |
| 13.60 | 6.51 | W |
| 16.67 | 5.31 | M |
| 19.31 | 4.59 | WM |
| 20.92 | 4.24 | WM |
| 22.00 | 4.04 | W |
| 22.56 | 3.94 | WM |
| 27.46 | 3.24 | W |
| 28.73 | 3.10 | W |
| 32.32 | 2.77 | W |

[a]±0.2

In preparing SSZ-59 zeolites, a N-methyl-N-[(1-phenylcyclopentyl)methyl]heptamethyleneiminium cation, N-methyl-N-[(1-(4-chlorophenyl)cyclopentyl)methyl] heptamethyleneiminium cation, N-methyl-N-[(1-phenylcyclopentyl)methyl]hexamethyleneiminium cation, N-methyl-N-[(1-(4-chlorophenyl)cyclopentyl)methyl] hexamethyleneiminium cation, N-methyl-N-((1-phenylcyclopentyl)methyl]piperidinium cation or N-methyl-N-[(1-(4-chlorophenyl)cyclopentyl)methyl] piperidinium cation is used as a crystallization template. In general, SSZ-59 is prepared by contacting an active source of one or more oxides selected from the group consisting of monovalent element oxides, divalent element oxides, trivalent element oxides, and tetravalent element oxides with the N-methyl-N-[(1-phenylcyclopentyl)methyl] heptamethyleneiminium cation, N-methyl-N-[(1-(4- chlorophenyl)cyclopentyl)methyl]heptamethyleneiminium cation, N-methyl-N-[(1-phenylcyclopentyl)methyl] hexamethyleneiminium cation, N-methyl-N-[(1-(4-chlorophenyl)cyclopentyl)methyl]hexamethyleneiminium cation, N-methyl-N-((1-phenylcyclopentyl)methyl] piperidinium cation or N-methyl-N-[(1-(4-chlorophenyl)cyclopentyl)methyl]piperidinium cation templating agent.

SSZ-59 is prepared from a reaction mixture having the composition shown in Table 7 below.

TABLE 7

SSZ-59 Reaction Mixtures

| | Typical | Preferred |
|---|---|---|
| $YO_2/W_aO_b$ | >20 | 35–70 |
| OH—/$YO_2$ | 0.1–0.5 | 0.15–0.3 |
| Q/$YO_2$ | 0.05–0.5 | 0.1–0.2 |
| $M_{2/n}/YO_2$ | 0.02–0.04 | 0.1–0.25 |
| $H_2O/YO_2$ | 20–80 | 25–40 | where Y, W, a, b, M and n are as defined above, and Q is the SDA.

SSZ-59 as prepared has a mole ratio of an oxide selected from silicon oxide, germanium oxide and mixtures thereof to an oxide selected from aluminum oxide, gallium oxide, iron oxide, boron oxide, titanium oxide, indium oxide, vanadium oxide and mixtures thereof greater than about 20; and has, after calcination, the X-ray diffraction lines of Table 10 below. SSZ-59 further has a composition, as synthesized (i.e., prior to removal of the templating agent from the zeolite) and in the anhydrous state, in terms of mole ratios, shown in Table 8 below.

TABLE 8

As-Synthesized SSZ-59

| | |
|---|---|
| $YO_2/W_cO_d$ | >20 |
| $M_{2/n}/YO_2$ | 0.01–0.03 |
| Q/$YO_2$ | 0.02–0.05 | where Y, W, c, d, M and n are as defined above, and Q is the SDA.

SSZ-59 zeolites, as-synthesized, have a crystalline structure whose X-ray powder diffraction pattern exhibit the characteristic lines shown in Table 9 and is thereby distinguished from other zeolites.

TABLE 9

As-Synthesized SSZ-59

| 2 Theta[a] | d | Relative Intensity |
|---|---|---|
| 6.1 | 14.5 | M |
| 7.2 | 12.3 | S |
| 8.3 | 10.6 | S |
| 14.4 | 6.14 | W |
| 15.7 | 5.64 | W |
| 17.1 | 5.18 | W |
| 18.45 | 4.80 | W |
| 20.75 | 4.28 | VS |
| 22.45 | 3.96 | M |
| 25.3 | 3.52 | M |
| 27.5 | 3.24 | W |
| 35.75 | 2.51 | W |

[a] ± 0.2

Table 9A below shows the X-ray powder diffraction lines for as-synthesized SSZ-59 including actual relative intensities.

TABLE 9A

| Two Theta[a] | d-spacing (Å) | Intensity I/Io × 100 |
|---|---|---|
| 6.07 | 14.54 | 37 |
| 7.20 | 12.26 | 45 |
| 8.28 | 10.68 | 55 |
| 14.42 | 6.140 | 12 |
| 15.71 | 5.638 | 6 |
| 16.72 | Sh 5.298 | 5 |
| 17.10 | 5.181 | 14 |
| 17.93 | Sh 4.942 | 3 |
| 18.24 | Sh 4.860 | 9 |
| 18.46 | 4.804 | 11 |
| 19.33 | 4.589 | 3 |
| 20.75 | 4.278 | 100 |
| 21.31 | Sh 4.165 | 6 |
| 21.95 | 4.047 | 7 |
| 22.45 | 3.957 | 24 |
| 22.99 | 3.866 | 3 |
| 24.76 | 3.593 | 10 |
| 25.30 | 3.517 | 18 |
| 25.54 | Sh 3.485 | 14 |
| 26.23 | 3.395 | 8 |
| 27.22 | Sh 3.274 | 7 |
| 27.47 | 3.244 | 15 |
| 29.09 | 3.067 | 2 |
| 29.67 | 3.009 | 3 |
| 30.21 | 2.956 | 6 |
| 31.09 | 2.875 | 5 |
| 32.17 | 2.780 | 6 |
| 33.05 | 2.708 | 2 |
| 33.55 | 2.669 | 2 |
| 34.48 | 2.599 | 4 |
| 35.76 | 2.509 | 15 |
| 37.00 | 2.427 | 2 |

[a] ± 0.2

After calcination, the SSZ-59 zeolites have a crystalline structure whose X-ray powder diffraction pattern include the characteristic lines shown in Table 10.

TABLE 10

Calcined SSZ-59

| 2 Theta[a] | d | Relative Intensity |
|---|---|---|
| 6.1 | 14.5 | VS |
| 7.2 | 12.3 | VS |
| 8.3 | 10.6 | VS |
| 15.7 | 5.64 | W |
| 17.1 | 5.18 | M |
| 18.5 | 4.79 | W |
| 20.7 | 4.29 | S |
| 22.4 | 3.97 | W |
| 25.2 | 3.53 | M |
| 27.5 | 3.24 | W |
| 35.6 | 2.52 | W |

[a] ± 0.2

Table 10A below shows the X-ray powder diffraction lines for calcined SSZ-59 including actual relative intensities.

TABLE 10A

| Two Theta (deg.)[a] | d-spacing (Å) | Intensity I/Io × 100 |
|---|---|---|
| 6.11 | 14.46 | 87 |
| 7.20 | 12.27 | 74 |
| 8.28 | 10.67 | 100 |
| 10.54 | 8.391 | 2 |
| 15.69 | 5.642 | 5 |
| 17.09 | 5.185 | 12 |
| 18.24 | Sh 4.859 | 5 |
| 18.53 | 4.785 | 10 |

TABLE 10A-continued

| Two Theta (deg.)[a] | d-spacing (Å) | Intensity I/Io × 100 |
|---|---|---|
| 19.28 | 4.600 | 3 |
| 20.71 | 4.286 | 65 |
| 21.50 | Sh 4.129 | 2 |
| 21.90 | Sh 4.055 | 3 |
| 22.40 | 3.966 | 16 |
| 24.11 | 3.688 | 2 |
| 24.84 | Sh 3.581 | 7 |
| 25.24 | 3.526 | 20 |
| 25.53 | Sh 3.486 | 11 |
| 26.20 | 3.399 | 4 |
| 27.19 | Sh 3.277 | 2 |
| 27.53 | 3.237 | 7 |
| 29.66 | 3.009 | 2 |
| 30.22 | 2.955 | 3 |
| 32.14 | 2.783 | 3 |
| 33.02 | 2.711 | 2 |
| 34.49 | 2.599 | 1 |
| 35.64 | 2.517 | 9 |
| 36.83 | 2.439 | 2 |
| 37.11 | 2.421 | 1 |
| 39.56 | 2.277 | 1 |

[a]0.2

Calcination can result in changes in the intensities of the peaks as well as minor shifts in the diffraction pattern. The zeolite produced by exchanging the metal or other cations present in the zeolite with various other cations (such as $H^+$ or $NH_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

The zeolites prepared by the present process are useful in hydrocarbon conversion reactions. Hydrocarbon conversion reactions are chemical and catalytic processes in which carbon-containing compounds are changed to different carbon-containing compounds. Examples of hydrocarbon conversion reactions include catalytic cracking, hydrocracking, dewaxing, alkylation, isomerization, olefin and aromatics formation reactions, and aromatics isomerization.

The following examples demonstrate, but do not limit, the present invention.

EXAMPLES

There are numerous variations on the embodiments of the present invention illustrated in the Examples which are possible in light of the teachings supporting the present invention. It is therefore understood that within the scope of the following claims, the invention may be practiced otherwise than as specifically described or exemplified.

Example A

Synthesis of Trimethyl[(phenylcyclopentyl)methyl] ammonium Hydroxide (SDA No. 13)

This example illustrates the general procedure for synthesizing the quaternary ammonium cation SDA's of the present invention.

Alkylation of Benzyl Nitrile

A 3-neck 1000-ml volume reaction flask is charged with 300 ml of anhydrous tetrahydrofuran (THF) and 47.5 gm (0.47 mol) of anhydrous diisopropylamine. To the solution, 180 ml of 2.5M solution of n-butyl lithium in hexane (0.448 mole nBuLi) is added slowly at −78° C. (dry ice-isopropyl alcohol bath) while stirring. Once the addition of nBuLi is complete, the mixture is allowed to stir for an additional 30 min. at −78° C. To the resulting solution (Lithium diisopropyl amide in THF and Hexane) at −78° C., 25 gm (0.213 mol) of benzyl nitrile in 50 ml THF is added drop-wise (via an addition funnel) while stirring. The resulting bright orange solution is allowed to further stir at −78° C. for about 1 hour. Then, to this solution (at −78° C.) 68 gm (0.22 mol) of 1,4-diiodobutane is added. The resulting mixture is warmed gradually to room temperature and further stirred over night. The reaction mixture is diluted with 500 ml ether and transferred to a 2000 ml separatory funnel. The mixture is washed three time with water (400 ml each) and once with brine solution. The ether layer is dried over anhydrous $MgSO_4$, filtered and concentrated, at reduced pressure on a rotary evaporator, to give 35.4 gm (97% yield) of colorless oil whose NMR data is ideal for the desired phenylcyclopentane carbonitrile.

Reduction of Phenylcyclopentane Carbonitrile to the Corresponding Primary Amine

To a stirring (mechanical stirring) suspension of 12 gm (0.315 mol) of lithium aluminum hydride in THF (600 ml) in a 2000 ml reaction flask at 0° C. (ice-bath), 35 gm (0.20 mol) of phenylcyclopentane carbonitrile in 100 ml THF is added dropwise via an addition funnel. The ice bath is replaced with a heating mantle and the reaction is heated at reflux for 16 hours. The reaction mixture is diluted with 500 ml ether and cooled down to 0° C. The reaction is worked up by adding 50 ml of 15 wt. % NaOH aqueous solution dropwise with vigorous stirring. Then 20 ml water is added and the mixture is stirred for an addition 10 minutes. The resulting two-phase mixture (a colorless liquid and a white precipitate) is filtered and the filtrate dried over anhydrous $MgSO_4$. Filtration and concentration at reduced pressure on a rotary evaporator gave 33 gm of [(phenylcyclopentyl)methyl]amine.

Quaternization of [(phenylcyclopentyl)methyl]amine With Methyl Iodide

To a stirred solution of 32 gm (0.18 mole) of [(phenylcyclopentyl)methyl]amine and 45 gm (0.45 mol) of potassium bicarbonate in 400 ml anhydrous methanol, 102 gm (0.72 mole) of methyl iodide is added. The reaction is mechanically stirred for 42 hours at room temperature. The reaction mixture is concentrated under reduced pressure on a rotary evaporator to give an off-white-colored solid material. The solids are rinsed several times with chloroform and filtered after each rinse. All the chloroform rinses are combined and concentrated to give a white powder whose NMR data is acceptable for the desired quaternary ammonium iodide salt. The reaction afforded 59 gm (95% yield) of the product. The iodide salt is purified by re-crystallization from isopropyl alcohol. This is done by completely dissolving the iodide salt in isopropyl alcohol and, then, precipitated by the addition of ethyl ether to the alcoholic solution. The procedure gives 55 gm of white powder with very clean $^1H$ and $^{13}C$-NMR NMR spectra for the product (trimethyl [(phenylcyclopentyl)methyl]ammonium iodide).

Ion Exchange of Trimethyl[(phenylcyclopentyl)methyl] ammonium Iodide With Hydroxide Trimethyl[(phenylcyclopentyl)methyl]ammonium iodide salt (50 gm; 0.144 mol) is dissolved in 175 ml water in a 500-ml volume plastic bottle. To the solution, 65 gm of Ion-Exchange Resin-OH (BIO RAD® AH1-X8) is added and the mixture is stirred at room temperature overnight. The mixture is filtered and the solids are rinsed with additional 75 ml of water. The original filtrate and the rinse are combined and a small amount is titrated with 0.1N HCl to indicate the presence of 0.14 mmol hydroxide (0.14 mmol of trimethyl((phenylcyclopentyl)methyl)ammonium hydroxide) in the solution.

The quaternary ammonium cation SDA's shown in Table A above are prepared in a similar manner.

SSZ-53

Example B

Synthesis of Trimethyl[(1-(4-fluorophenyl) cyclopentyl)methyl]ammonium Cation (SDA No. 17)

In a 2 Liter volume three-necked round bottom reaction flask equipped with a mechanical stirrer and reflux condenser with a drying tube, 15 grams (0.4 mole) of lithium aluminum hydride (95% purity; Aldrich) is suspended in 400 ml anhydrous tetrahydrofuran (THF; Aldrich) and stirred at room temperature for 15 minutes. The dark gray suspension is cooled down to 0° C. by means of an ice-bath. To the suspension 25 gm (0.132 mole) of 1-(4-fluoruphenyl) cyclopentylcarbonitrile (ACROS ORGANICS) in 50 ml anhydrous THF is added drop wise via an addition funnel. Once the addition is complete, the ice bath is replaced with a heating mantle, and the reaction mixture is refluxed over night. The reaction mixture is cooled down to 0° C. (ice-bath) and diluted with 500-ml ethyl ether. The reaction is worked up by adding 60 ml of 15% w/w aqueous solution of NaOH drop wise (via an addition funnel) with vigorous stirring. Then, 15 ml water is added and the reaction is allowed to stir for an additional 30 minutes and then allowed to settle. The milky solution quickly turns into a colorless liquid layer and a fine white powder, which precipitates to the bottom of the flask. The reaction mixture is filtered and the solids are thoroughly rinsed with ethyl ether. The ether filtrates are combined and dried over $MgSO_4$, filtered and concentrated to give 24.5 grams of colorless oil whose $^1$H-NMR and $^{13}$C-NMR data are acceptable for the expected amine; [1-(4-fluorophenyl)cyclopentyl]methyl amine.

Quaternization: The obtained [1-(4-fluorophenyl) cyclopentyl]methyl amine. (24 gm; 0.124 mole) is dissolved in 300 ml methanol (ACS reagent). To this solution, 38 gm (0.375 mole) of $KHCO_3$ and 80 gm (0.56 mole) of methyl iodide are added and the resulting mixture is stirred at room temperature for 48 hours and then is heated at reflux for 6 hours. The resulting cloudy solution is concentrated under reduced pressure on a rotary evaporator to give a white solid material. The solids are rinsed several times with chloroform and filtered after each rinse. All the rinses are combined and concentrated to give a white powder whose NMR data are agreeable for the desired quaternary ammonium iodide salt. The reaction affords 40.5 gm (90% yield) of the product. Recrystallization of the powder from isopropyl alcohol gives 38 gm of pure trimethyl[(!-(4-fluorophenyl)cyclopentyl) methyl]ammonium iodide salt as shinny white flakes.

Ion Exchange: The obtained trimethyl[(1-(4-fluorophenyl)cyclopentyl)methyl]ammonium iodide salt (37 gm; 0.1 mol) is dissolved in 120 ml water in a 500-ml volume plastic bottle. To the solution, 130 gm of Ion-Exchange Resin (BIO RAD®) AG1-X8 ion exchange resin, hydroxide form) is added and the mixture is stirred at room temperature overnight. The mixture is filtered and the solids are rinsed with additional 80 ml of water. The original filtrate and the rinse are combined and a small aliquot is titrated with 0.1N HCl to indicate the presence of 95 mmol hydroxide (95 mmol template SDA No. 17) in the solution.

Examples 1–4

Preparation of Borosilicate SSZ-53

Starting $SiO_2/B_2O_3$=46

The table below summarizes the crystallization experiments and data for the different SDA's No. 17, 16, 15 and 14 used in the synthesis of SSZ-53. In a typical run, 3 mmol of the templating agent, 1.2 mmol of NaOH, 0.16 mmol of sodium borate decahydrate ($Na_2B_4O_7 \cdot 10H_2O$) and 14.8 mmol of $SiO_2$ (0.9 gm of CAB-O-SIL® M-5 amorphous fumed silica) are mixed in 11.25 gm of de-ionized water (625 mmol) in a 23 cc Teflon liner. The components are thoroughly mixed in the liner and the resulting gel is capped off and placed in a Parr reactor and heated in an oven at 160° C. while rotating at 43 rpm. The reaction is monitored by checking the gel's pH, and by looking for crystal formation using Scanning Electron Microscopy (SEM) every six days. The reaction is usually completed within 12–21 days. The resulting reaction mixture is then filtered through a fritted-glass funnel, and the collected solids are washed several times with water (a total of 1 liter) and allowed to air-dry over night. The solid product is further dried in an oven at 120 C. for 1 hour. The typical yield is 80–90% (based on the starting solid mass). The product is then analyzed and characterized by TEM and powder XRD.

| Example | SDA | $SiO_2/$ $B_2O_3$ | $SiO_2/$ —OH | $SiO_2/$ Na | $H_2O/$ $SiO_2$ | Time (days) | Product |
|---|---|---|---|---|---|---|---|
| 1 | 17 | 46 | 3.5 | 9.7 | 42 | 18 | SSZ-53 |
| 2 | 16 | 46 | 3.5 | 9.7 | 42 | 18 | SSZ-53 |
| 3 | 15 | 46 | 3.5 | 9.7 | 42 | 21 | SSZ-53 |
| 4 | 14 | 46 | 3.5 | 9.6 | 42 | 12 | SSZ-53 |

Analysis by XRD shows the product to be SSZ-53.

In a similar manner, SSZ-53 is prepared using in turn SDA' No. 18, 19, 20, 22, 23 and 32.

Example 5

Preparation of Aluminosilicate SSZ-53

Starting $SiO_2/Al_2O_3$=70 With SDA No. 13

To a solution of trimethyl[(phenylcyclopentyl)methyl] ammonium hydroxide (~3 mmol; 7.5 gm of 0.40 molar SDA No. 13 solution) and 0.75 mmol NaOH (0.75 gm of 1 N aqueous solution) in a 23 cc Teflon cup, a 0.25 gm of sodium-Y zeolite (Union Carbide's LZ-210) and 0.75 gm of CAB-O-SIL® M-5, amorphous fumed silica are added, consecutively. The mixture is thoroughly stirred and the resulting gel is capped off and placed in a Parr reactor and heated in an oven at 160° C. while rotating at 43 rpm. The reaction is monitored by checking the gel's pH, and by looking for crystal formation using Scanning Electron Microscopy (SEM) at six day intervals. The reaction is completed after heating at the temperature described above (while rotating at 43 rpm)) for 12 days. The reaction mixture appears as a paste, which is crystalline by SEM analysis. The paste is diluted with de ionized water and filtered through a fritted-glass funnel. The resulting solid is washed generously with water and allowed to air-dry over night to yield 1.0 gm of a fine white powder. The material is found to be SSZ-53 by XRD. A trace amount of unconverted LZ-210 is also present in the powder as indicated by XRD Example 6

Seeded Preparation of Borosilicate SSZ-53

The reactions described in Examples 1–4 are repeated, with the exception of seeding with 0.05 gram of SSZ-53 crystals. In this case, SSZ-53 is obtained in 6–8 days.

Example 7

Preparation of Borosilicate SSZ-53 at Varying $SiO_2/B_2O_3$ Ratios

Three mmol of a solution of SDA No. 17 (6.67 grams, 0.45 mmol OH⁻/g) is mixed with 1.2 grams of 1.0 N NaOH and 4.15 grams of water. Sodium borate decahydrate (0.01–0.12 gram) is added to this solution and stirred until all of the solids have dissolved. CAB-O-SIL® M-5, amorphous fumed silica (0.9 gram, about 14.7 mmol $SiO_2$) is then added to the solution and the resulting mixture is heated at 160 C. and rotated at 43 rpm for 12–30 days. The products of each of the reactions is filtered, washed, dried and determined by XRD analysis.

The data presented in the table below is obtained from attempts aimed at making SSZ-53 (borosilicate) at different $SiO_2/B_2O_3$ ratios while keeping the ratio of $SiO_2$ to other reagents constant using SDA No. 17 as the structure-directing agent.

| $SiO_2/B_2O_3$ | XRD results |
| --- | --- |
| 282 | Cristobalite (major), SSZ-53 (minor) |
| 141 | Cristobalite (major), SSZ-53 (minor) |
| 94 | SSZ-53 |
| 70.5 | SSZ-53 |
| 56 | SSZ-53 |
| 47 | SSZ-53 |
| 40.25 | SSZ-53 |
| 35.25 | SSZ-53 |
| 31.3 | SSZ-53 |
| 28.2 | SSZ-53 |
| 25.5 | SSZ-53 |
| 23.5 | SSZ-53 |

$SiO_2$/OH for all runs is 3.5; $SiO_2$/Na for all runs is 12.3 and $H_2O/SiO_2$ for all runs is 42.

The data presented in the table below is obtained from attempts aimed at making SSZ-53 (borosilicate) at different $SiO_2/B_2O_3$ ratios while keeping the ratio of $SiO_2$ to other reagents constant using SDA No. 13 as the structure-directing agent.

| $SiO_2/B_2O_3$ | XRD results |
| --- | --- |
| 282 | Cristobalite |
| 141 | Cristobalite |
| 94 | Cristobalite, SSZ-53 (trace) |
| 70.5 | Cristobalite, SSZ-53 (minor) |
| 56 | SSZ-53 |
| 47 | SSZ-53 |
| 40.25 | SSZ-53 |
| 35.25 | SSZ-53 |
| 31.3 | SSZ-53 |
| 28.2 | SSZ-53 |
| 25.5 | SSZ-53 |
| 23.5 | SSZ-53 |

$SiO_2$/OH for all runs is 3.5; $SiO_2$/Na for all runs is 12.3 and $H_2O/SiO_2$ for all runs is 42.

SSZ-55

Example C

Synthesis of Trimethyl[(1-(3-fluorophenyl)cyclopentyl)methyl]ammonium Cation (SDA No. 16)

In a 2-liter volume three-necked round bottom reaction flask equipped with a mechanical stirrer and reflux condenser with a drying tube, 18 grams (0.47 mole) of lithium aluminum hydride (95% purity; Aldrich) is suspended in 500 ml anhydrous tetrahydrofuran (THF: Aldrich) and stirred at room temperature for 15 minutes. The dark gray suspension is cooled down to 0° C. (ice-bath) and 25 gm (0.132 mole) of 1-(3-fluorophenyl)cyclopentylcarbonitrile (ACROS ORGANICS) in 50 ml anhydrous THF is added drop wise via an addition funnel.

Once the addition is complete, the ice bath is replaced with a heating mantle, and the reaction mixture is refluxed over night. The reaction mixture is cooled down to 0° C. (ice-bath) and diluted with 500 ml ethyl ether. The reaction is worked up by adding 70 ml of 15% w/w aqueous solution of NaOH drop wise (via an addition funnel) with vigorous stirring. Then, 15 ml water is added and the reaction is allowed to stir for an additional 30 minutes and then allowed to settle. The milky solution quickly turns into a colorless liquid layer and a fine white powder, which precipitates to the bottom of the flask. The solution is filtered and the solids are thoroughly rinsed with ethyl ether. The ether filtrates are combined and dried over $MgSO_4$, filtered and concentrated to give 29 grams of colorless oil whose $^1$H-NMR and 13C-NMR data are ideal for the expected [1-(3-fluorophenyl)cyclopentyl]methyl amine.

Quaternization: [1-(3-fluorophenyl)cyclopentyl]methyl amine (28 gm; 0.146 mole) is dissolved in 400 ml methanol (ACS reagent). To this solution, 44 gm (0.44 mole) of $KHCO_3$ and 93.6 gm (0.66 mole) of methyl iodide are added and the resulting mixture is stirred at room temperature for 48 hours and then heated at reflux overnight. Concentration of the reaction mixture under reduced pressure on a rotary evaporator gives a solid material, which is rinsed several times with chloroform and filtered after each rinse. All the chloroform rinses are combined and concentrated to give a white powder whose NMR data are acceptable for the desired quaternary ammonium iodide salt. The reaction affords 49 gm (92% yield) of the product. Recrystallization of the powder from isopropyl alcohol gives 43 gm of trimethyl[(1-(3-fluorophenyl)cyclopentyl)methyl] ammonium iodide as shinny white flakes.

Ion Exchange: Trimethyl[(1-(3-fluorophenyl)cyclopentyl)methyl]ammonium iodide salt (40 gm; 0.11 mol) is dissolved in 140 ml water in a 500-ml volume plastic bottle. To the solution, 130 gm of Ion-Exchange Resin-OH (BIO RAD® AG1-X8) is added and the mixture is stirred at room temperature overnight. The mixture is filtered and the solids are rinsed with additional 100 ml of water. The original filtrate and the rinse are combined and a small aliquot is titrated with 0.1 N HCl to indicate the presence of 96 mmol hydroxide (96 mmol SDA No. 16) in the solution.

The synthesis of trimethyl[((phenylcyclobutyl)methyl]ammonium cation (SDA No. 12) is accomplished using the same methodology described in Example C above for the preparation of SDA No. 16 starting from 1-phenylcyclobutylcarbonitrile.

Example 8

Preparation of Borosilicate SSZ-55

Starting $SiO_2/B_2O_3$=35 With SDA No. 16

To a mixture of trimethyl[(1-(3-fluorophenyl)cyclopentyl)methyl]ammonium hydroxide (3 mmol; 7.5 gm of 0.4 molar SDA No. 16 solution), 1.2 mmol NaOH (1.2 gm of 1 N aqueous solution) and 3.3 gm of water in a 23 cc Teflon cup, a 0.08 gm of sodium borate decahydrate ($Na_2B_4O_7 \cdot 10\ H_2O$) are added and stirred until completely dissolved. To this solution, 0.9 gm of CAB-O-SIL® M-5 amorphous fumed silica is added as a source of $SiO_2$ and the mixture is thoroughly stirred. The resulting gel is capped off and placed in a Parr reactor and heated in an oven at 160° C. while rotating at 43 rpm.

The reaction is monitored by checking the gel's pH, and by looking for crystal formation using Scanning Electron Microscopy (SEM) every six days. The reaction is completed after heating at the temperature described above (while rotating at 43 rpm)) for 12 days. The reaction mixture appears as a colorless liquid with fine white solid settled at the bottom of the Teflon liner. The mixture is filtered through a fritted-glass funnel, and the obtained white solids are washed several times with water (a total of 1 liter) and, then, allowed to air-dry over night to yield 0.84 gram of a fine white powder. SEM indicates the presence of only one crystalline phase. Analysis by XRD shows the product to be SSZ-55.

Example 9

Preparation of Aluminosilicate SSZ-55

Starting $SiO_2/Al_2O_3=35$ With SDA No. 12

To a mixture of trimethyl[(phenylcyclobutyl)methyl] ammonium hydroxide (2.25 mmol; 5.9 gm of 0.38 molar SDA No. 12 solution), 1.5 mmol NaOH (1.5 gm of 1 N aqueous solution) in a 23 cc Teflon cup, 0.26 gm of sodium-Y zeolite (Union Carbide's LZ-Y52) and 0.81 gm of CAB-O-SIL® M-5 amorphous fumed silica are added, consecutively. The mixture is thoroughly stirred and the resulting gel is capped off and placed in a Parr reactor and heated in an oven at 160° C. while rotating at 43 rpm.

The reaction is monitored by checking the gel's pH, and by looking for crystal formation using Scanning Electron Microscopy (SEM) at six days intervals. The reaction is completed after heating at the temperature described above (while rotating at 43 rpm) for 12 days. The reaction mixture appears as a colorless liquid with fine white solid settled at the bottom of the Teflon liner. The mixture is filtered through a fritted-glass funnel, and the obtained white solids are washed generously with water and, then, are allowed to air-dry over night to yield 1.02 gm of a fine white powder. The material is found to be SSZ-55 by XRD.

Example 10

Seeded Preparation of Borosilicate SSZ-55

The reaction described in Example 8 is repeated, with the exception of seeding with 0.05 gram of SSZ-55 crystals. In this case, SSZ-55 is obtained in 7 days. The product has a $SiO_2/B_2O_3$ mole ratio of 31.

Example 11

Preparation of Aluminosilicate SSZ-55 at Varying $SiO_2/Al_2O_3$ Ratios

The reaction described in Example 9 is repeated, with the exception that varying amounts (0.07 gm–0.26 gm) of Na-Y zeolite (Union Carbides LZ-Y52) are used. After 12–18 days at 160° C. and 43 rpm, the isolated products are determined by XRD to be SSZ-55.

The table below shows the results obtained from carrying out the synthesis of SSZ-55 at varying $SiO_2/Al_2O_3$ ratios in the synthesis gel using SDA No. 12 as the structure-directing agent. As indicated in the column of results, the synthesis leads to SSZ-55 in all gel compositions, but contaminated with starting Na-Y impurities in all the runs.

| $SiO_2/Al_2O_3$ | $SiO_2/Na$ | XRD results |
| --- | --- | --- |
| 36 | 6.67 | SSZ-55 (major), Na-Y (minor), ANA (trace) |
| 38 | 6.67 | SSZ-55 (major), Na-Y (minor), ANA (trace) |
| 41.7 | 6.67 | SSZ-55 (major), Na-Y (minor) |
| 44.2 | 6.74 | SSZ-55 (major), Na-Y (minor), ANA (trace) |
| 47.9 | 7.45 | SSZ-55 (major), Na-Y (minor) |
| 51.1 | 7.21 | SSZ-55 (major), Na-Y (minor) |
| 61.6 | 6.99 | SSZ-55 (major), Na-Y (minor) |
| 80 | 7.37 | SSZ-55 (major), Na-Y (minor) |
| 100.4 | 7.66 | SSZ-55 (major), Na-Y (minor) |

$SiO_2/OH$ for all runs is 4.23; $H_2O/SiO_2$ for all runs is 27.

Example 12

Preparation of Borosilicate SSZ-55 at Varying $SiO_2/BO3$ Ratios

Three mmol of a solution of SDA No. 16 (7.5 grams, 0.4 mmol $OH^-/g$) is mixed with 1.2 grams of 1.0 N NaOH and 3.3 grams of water. Sodium borate decahydrate (0.01–0.12 gram) is added to this solution and stirred until all of the solids have dissolved. CAB-O-SIL® M-5 amorphous fumed silica (0.9 gram, about 14.7 mmol $SiO_2$) is then added to the solution and the resulting mixture is heated at 160° C. and rotated at 43 rpm for 12–24 days. A settled product results, which is filtered, washed, dried and determined by XRD to be SSZ-55.

The data presented in the table below is obtained from attempts aimed at making SSZ-55 (borosilicate) at different $SiO_2/B_2O_3$ ratios while keeping the ratio of $SiO_2$ to other reagents constant using SDA No. 16 as the structure-directing agent.

| $SiO_2/B_2O_3$ | $SiO_2/Na$ | XRD results |
| --- | --- | --- |
| 140.16 | 12.3 | Cristobalite |
| 70.08 | 12.3 | Cristobalite |
| 46.72 | 12.3 | No SSZ-55 product |
| 35.04 | 12.3 | unknown zeolite |
| 28.03 | 12.3 | unknown zeolite |
| 23.36 | 12.3 | Unknown zeolite (mostly), SSZ-55 (trace) |
| 20.02 | 12.3 | SSZ-55 (mostly), unknown zeolite (trace) |
| 17.52 | 12.3 | SSZ-55 |
| 15.57 | 12.3 | SSZ-55 |
| 14.02 | 12.3 | SSZ-55 |
| 12.74 | 12.3 | SSZ-55 |
| 11.68 | 12.3 | SSZ-55 |

$SiO_2/OH$ for all runs is 3.5; $H_2O/SiO_2$ for all runs is 42.

SSZ-59

Example D

Synthesis of N-methyl-N-[(1-phenylcyclopentyl)methyl]piperidinium Cation (SDA No. 29)

The templating agent was synthesized from the commercially available starting materials according to the synthetic sequence scheme shown below.

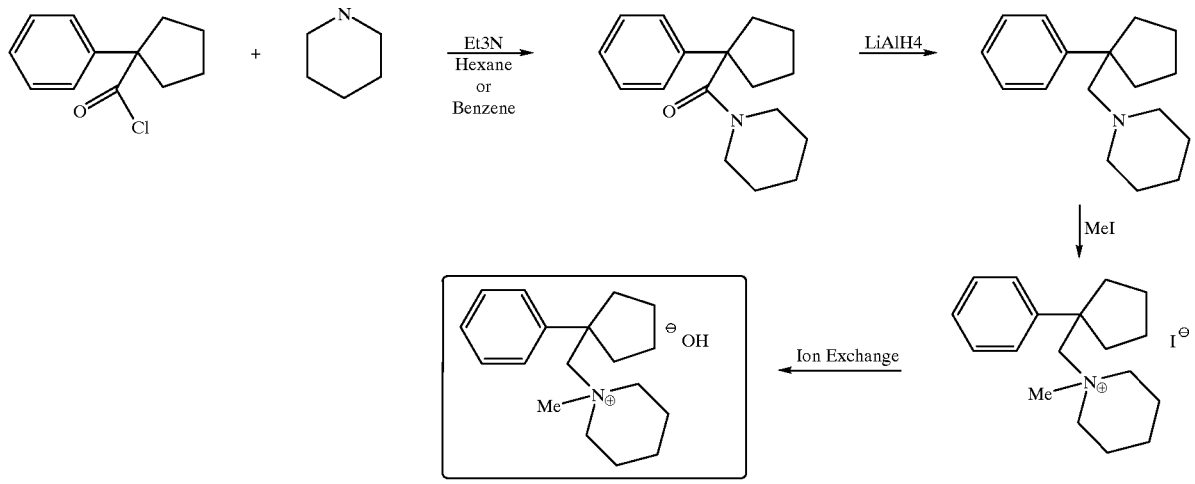

Synthesis of the Starting Amide(Phenylcyclopentyl Piperidyl Ketone)

To a mechanically stirred solution of piperidine (85.15 gm; 1 mole) and triethylamine (126.5 gm; 1.25 mole) in 800 ml anhydrous benzene in a 2-liter three-neck round bottom reaction a 215 gm (1.03 mole) of 1-phenylcyclopentanecarbonyl chloride (synthesis of this compound is described below), dissolved in 100 ml benzene, were added drop wise via an addition funnel at 0° C. over a period of 20 minutes. The resulting mixture (a solution with tan-colored solids) was allowed to gradually warm up to room temperature and continued to stir over night. The resulting Mixture was transferred to a 2-liter separatory funnel and diluted with 600 ml ethyl acetate. The mixture was washed three times with water (300 ml each) and once with 300 ml saturated sodium chloride solution. The organic phase was dried over anhydrous magnesium sulfate, filtered and concentrated at reduced pressure on a rotary evaporator to give 241 gm of the desired amide (pure by NMR analysis) as a tan-colored solid.

Reduction of Phenylcyclopentyl Piperidyl Ketone to the Corresponding N-[(1-phenylcyclopentyl)methyl]piperidine To a mechanically stirred suspension of lithium aluminum hydride (37.95 gm; 1 mole) in 1000 ml anhydrous tetrahydrofuran (THF) at 0° C. (ice-water bath) in a 2-liter 3-neck flask, the amide (128.7 gm, 0.5 mole) dissolved in 200 ml anhydrous THF was added drop-wise via an addition funnel. Once the addition was completed, the ice-water bath was removed and the reaction was stirred for 0.5 hrs at room temperature. The reaction was, then, heated at reflux for 3 hrs. The heat source was removed and once the reaction mixture cooled down to room temperature, the mixture was cooled to 0° C. by means of an ice-water bath. The mixture was diluted with 500 ml ethyl ether and the reaction was worked up by adding 225 ml of 15% aqueous NaOH solution drop-wise via an addition funnel. The resulting bi-phasic (colorless liquid and white precipitate) solution was filtered though a fritted-glass funnel The filtrate was dried over anhydrous magnesium sulfate, filtered and concentrated at reduced pressure on a rotary evaporator to give 118 gm of the desired amine (pure by NMR analysis) as a pale yellow oil.

Quaternization (Synthesis of N-methyl-N-[(1-phenylcyclopentyl)methyl]piperidinium Iodide)

To a mechanically stirred solution of [(1-phenylcyclopentyl)methyl]piperidine (115 gm; 0.47 mole) in 1000 ml methanol (ACS reagent), methyl iodide (100 gm; 0.7 mole) were added. The resulting mixture was stirred for 48 hrs. Then an additional 35 gm (0.5 mole equivalent) of methyl iodide was added and the reaction was heated for 1 hr. The resulting solution was concentrated under reduced pressure on a rotary evaporator to give 175 gm of a tan solid material. The obtained solid was re-crystallized by dissolving in hot isopropyl alcohol and allowed to re-crystallize overnight. Re-crystallization afforded 171 gm of the product (NMR analysis) as shinny white needles.

Ion Exchange (Making N-methyl-N-[(1-phenylcylopentyl)methyl]piperidinium Hydroxide)

To a gently stirred solution of 100 gm (0.26 mole) of methyl((phenylcyclopentyl)methyl)piperidinium iodide in 400 ml de-ionized water in a plastic bottle, 325 gm of Ion-Exchange Resin-OH (BIO RAD®) were added and the mixture was let to stir at room temperature overnight. The mixture was filtered through a fritted-glass funnel and the solids were rinsed with additional 75 ml of water. A small aliquot from the filtrate was titrated with 0.1N HCl to indicate a total yield of 0.22 mole of OH ions (hence 0.22 of N-methyl-N-[(1-phenylcyclopentyl)methyl]piperidinium hydroxide).

Synthesis of 1-Phenylcyclopentanecarbonyl Chloride

The carboxylic acid chlorides used in the synthesis of the parent amides were all synthesized as described below. In a 1-liter 3-neck flask, 200 gm (1.05 mole) of 1-phenylcyclopentanecarboxylic acid (ACROS ORGANICS) was added drop-wise to stirring excess of thionyl chloride (Aldrich) under nitrogen. The resulting mixture was heated at reflux for two hrs. The reaction was further stirred at room temperature overnight. The resulting brown-red solution was concentrated at reduced pressure and heat on a rotary evaporator to remove excess thionyl chloride. The reaction yielded 216 gm of a lachrymator substance whose $^1$H-NMR and 13C-NMR spectra were ideal for the desired acid chloride.

Example E

Synthesis of Templating Agent N-methyl-N-[(1-(4-chlorophenyl)cyclopentyl)methyl]piperidinium Cation (SDA No. 24)

N-methyl-N-[(1-(4-chlorophenyl)cyclopentyl)methyl] piperidinium cation was synthesized using the above procedure starting from piperidine and 1-(4-chlorophenyl)cyclopentanecarbonyl chloride.

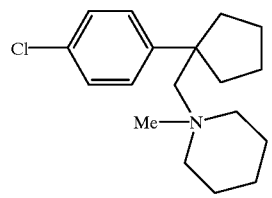

Example F

Synthesis of Templating Agent N-methyl-N-[(1-phenylcyclopentyl)methyl]heptamethyleneiminium Cation (SDA No. 30)

N-methyl-N-[(1-phenylcyclopentyl)methyl]heptamethyleneiminium cation was synthesized using the above procedure starting from heptametheleneimine and 1-phenylcyclopentanecarbonyl chloride

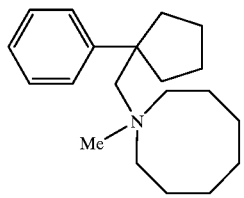

Example G

Synthesis of N-methyl-N-[(1-(4-chlorophenyl)cyclopentyl)methyl]heptamethyleneiminium Cation (SDA No. 26)

N-methyl-N-[(1-(4-chlorophenyl)cyclopentyl)methyl]heptamethyleneiminium cation was synthesized using the above procedure starting from heptametheleneimine and 1-(4-chlorophenyl)cyclopentanecarbonyl chloride.

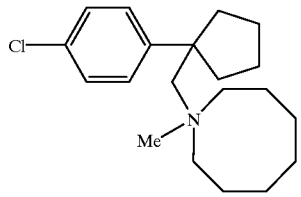

Example H

Synthesis of Templating Agent N-methyl-N-[(1-phenylcyclopentyl)methyl]hexamethyleneiminium Cation (SDA No. 25)

N-methyl-N-[(1-phenylcyclopentyl)methyl]hexamethyleneiminium cation was synthesized using the above procedure starting from hexametheleneimine and 1-phenylcyclopentanecarbonyl chloride

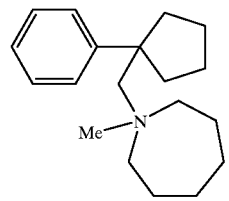

Example I

Synthesis of N-methyl-N-[(1-(4-chlorophenyl)cyclopentyl)methyl]hexamethyleneiminium Cation (SDA No. 35)

N-methyl-N-[(1-(4-chlorophenyl)cyclopentyl)methyl]hexamethyleneiminium cation was synthesized using the above procedure starting from hexametheleneimine and 1-(4-chlorophenyl)cyclopentanecarbonyl chloride

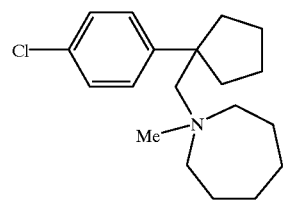

Example 13

Synthesis of Boron-SSZ-59

In a 23-cc Teflon liner, 6.48 gm of 0.46 M solution (aqueous) of SDA No. 24 methyl[(1-(4-chlorophenyl)cyclopentyl)methyl]piperidinium hydroxide (3 mmol) are mixed with 1.2 gm of 1.0N NaOH (1.2 mmol) and 4.3 gm of de-ionized water. To this mixture, 0.06 gm of sodium borate decahydrate is added and stirred until completely dissolved. To this mixture, 0.9 gm of CAB-O-SIL® M-5 amorphous fumed silica (about 14.7 mmol $SiO_2$) is added. The mixture is thoroughly stirred and the resulting gel is capped off and placed in a steel Parr autoclave and heated in an oven at 160° C. while tumbling at 43 rpm. The progress of the reaction is monitored by Scanning Electron Microscopy at intervals of 6 days. Once completed (after heating for 12 days), the pasty reaction mixture is filtered through a fritted glass funnel. The collected solid is rinsed with water (1 liter) and air-dried overnight. The solids are further dried in an oven at 120° C. for 2 hours. The reaction yielded 0.9 gm of SSZ-59 as a white powder.

The table below shows the synthesis of Boron-SSZ-59 at varying $SiO_2/B_2O_3$ ratios. The data presented in the table is obtained from attempts at making the borosilicate version of SSZ-59 at different $SiO_2/B_2O_3$ ratios while keeping $SiO_2$ to other reagent constant using SDA No. 24 as structure directing agent.

| $SiO_2/B_2O_3$ | XRD Results |
| --- | --- |
| 0 | Layered |
| 280 | Cristobalite |

-continued

| $SiO_2/B_2O_3$ | XRD Results |
|---|---|
| 140 | SSZ-59 |
| 93.3 | SSZ-59 |
| 70 | SSZ-59 |
| 56 | SSZ-59 |
| 46.7 | SSZ-59 |
| 40 | SSZ-59 |
| 35 | SSZ-59 |
| 31 | SSZ-59 |
| 28 | SSZ-59 |
| 25.5 | SSZ-59 |
| 23.5 | SSZ-59 |
| 20 | SSZ-59 |
| 18.7 | SSZ-59 |
| 15.6 | SSZ-59 |
| 14 | SSZ-59, Cristobalite |

$SiO_2/OH$ for all runs is 3.5; $H_2O/SiO_2$ for all runs is 44

Example 14

Synthesis of Aluminosilicate SSZ-59

In a 23-cc Teflon liner, 6.75 gm of 0.34 M solution (aqueous) of SDA 26 methyl[(1-(4-chlorophenyl)cyclopentyl)methyl]heptamethyleneiminium hydroxide (2.25 mmol) is mixed with 1.5 gm of 1.0N NaOH (1.5 mmol). To this mixture, 0.25 gm of Union Carbide's LZ-Y52 zeolite is added. Then, 0.8 gm of CAB-O-SIL® M-5 amorphous fumed silica (about 14.7 mmol $SiO_2$) is added. The mixture is thoroughly stirred and the resulting gel is capped off and placed in steel Parr autoclave and heated in an oven at 160° C. while tumbling at 43 rpm. The progress of the reaction is monitored by Scanning Electron Microscopy at intervals of 6 days. Once completed (after heating for 6 days), the pasty looking reaction mixture is filtered through a fritted glass funnel. The collected solid is rinsed with water (1 liter) and air-dried overnight. The solids are further dried in an oven at 120° C. for 2 hours. The reaction yields 0.75 gm of a white powder. Analysis by XRD shows the product to be SSZ-59.

SSZ-59 is made in a similar manner using SDA's No. 25, 29, 30, and 31 as the templating agent.

SSZ-48

Example 15

Synthesis of Boron-SSZ-48

A 23 cc Teflon liner is charged with 6.7 gm of 0.48M aqueous solution of SDA No. 11 trimethyl((phenylcyclopropyl)methyl)ammonium hydroxide (3 mmol SDA), 1.2 gm of 1M aqueous solution of NaOH (1.2 mmol NaOH) and 4.1 gm of de-ionized water. To this mixture, 0.06 gm of sodium borate decahydrate (0.157 mmol of $Na_2B_4O_7 \cdot 10H_2O$; about 0.315 mmol $B_2O_3$) is added and stirred until completely dissolved. Then, 0.9 gm of CAB-O-SIL® M-5, amorphous fumed silica, (about 14.7 mmol $SiO_2$) is added to the solution and the mixture is thoroughly stirred. The resulting gel is capped off and placed in a Parr bomb steel reactor and heated in an oven at 160° C. while rotating at 43 rpm. The reaction is monitored by checking the gel's pH, and by looking for crystal formation using Scanning Electron Microscopy at six days intervals. The reaction is completed after heating for 12 days at the conditions described above. Then, the resulting pasty mixture is filtered through a fritted-glass funnel. The collected solids are thoroughly washed with water and then rinsed with acetone (~10 ml) to remove any organic residues. The solids are allowed to air-dry over night and then dried in an oven at 120° C. for 1 hour. The reaction affords 0.85 gram of SSZ-48.

In a similar manner, SSZ-48 is prepared using in turn SDA's No. 12, 21 and 33.

ZSM-39

Example 16

Synthesis of Al-ZSM-39

A 23 cc Teflon liner is charged with 5 gm of 0.45M aqueous solution of SDA No. 6 N,N,N-trimethyl(2-ethyl-2-p-tolylbutyl)ammonium hydroxide (2.25 mmol SDA), 1.5 gm of 1M aqueous solution of NaOH (1.5 mmol NaOH) and 5.4 gm of de-ionized water. To this mixture, 0.035 gm of Reheis F-2000 alumina (0.53 wt % $Al_2O_3$) is added and stirred until completely dissolved. Then, 0.9 gm of CAB-O-SIL® M-5, amorphous fumed silica, (about 14.7 mmol $SiO_2$) is added to the solution and the mixture is thoroughly stirred. The resulting gel is capped off and placed in a Parr bomb steel reactor and heated in an oven at 170° C. while rotating at 43 rpm. The reaction is monitored by checking the gel's pH, and by looking for crystal formation using Scanning Electron Microscopy at six days intervals. The reaction is completed after heating for 18 days at the conditions described above. Then, the reaction mixture, comprising of a clear liquid layer with solids (powder) settled to the bottom of the Teflon liner, is filtered through a fritted-glass funnel. The collected solids are thoroughly washed with water and then rinsed with acetone (10 ml) to remove any organic residues. The solids are allowed to air-dry over night and then dried in an oven at 120° C. for 1 hour. The reaction affords 0.75 gram of ZSM-39.

In a similar manner, ZSM-39 is prepared using in turn SDA's No. 1, 2, 3, 4, 5, 7, 8, 9, 10, 27, and 28.

ZSM-12

Example 17

Synthesis of Boron-ZSM-12

A 23 cc Teflon liner is charged with 5.3 gm of 0.57M aqueous solution of SDA No. 27 trimethyl[(1-(4-methoxyphenyl)cyclohexyl)methyl]ammonium hydroxide (3 mmol SDA), 1.2 gm of 1M aqueous solution of NaOH (1.2 mmol NaOH) and 5.3 gm of de-ionized water. To this mixture, 0.062 gm of sodium borate decahydrate (0.157 mmol of $Na_2B_4O_7 \cdot 10H_2O$; about 0.315 mmol $B_2O_3$) is added and stirred until completely dissolved. Then, 0.9 gm of CAB-O-SIL® M-5, amorphous fumed silica, (about 14.7 mmol $SiO_2$) is added to the solution and the mixture is thoroughly stirred. The resulting gel is capped off and placed in a Parr bomb steel reactor and heated in an oven at 160° C. while rotating at 43 rpm. The reaction is monitored by checking the gel's pH, and by looking for crystal formation using Scanning Electron Microscopy at six days intervals. Once the reaction is complete (after heating for 12 days at the conditions described above), the resulting mixture, comprising a clear liquid layer with solids (powder) settled to the bottom of the Teflon liner, is filtered through a fritted-glass funnel. The collected solids are thoroughly washed with water and then rinsed with minimal amount of acetone to remove any organic residues. The solids are allowed to air-dry over night and then dried in an oven at 120° C. for 1 hour. The reaction affords 0.86 gram of ZSM-12.

ZSM-51

Example 18

Synthesis of ZSM-51

In a manner similar that described above, ZSM-51 is prepared using in turn SDA's No. 2, 3 and 5.

ZSM-48

Example 19

Synthesis of ZSM-48

In a manner similar that described above, ZSM-48 is prepared using SDA No. 6.

ZSM-5

Example 20

Synthesis of ZSM-5

In a manner similar that described above, ZSM-5 is prepared using in turn SDA's No. 8, 9, 10 and 27.

What is claimed is:

1. A process for preparing a zeolite which comprises:
    (a) preparing an aqueous solution from (1) sources of an alkali metal oxide, alkaline earth metal oxide or mixtures thereof; (2) sources of an oxide selected from the oxides of aluminum, iron, gallium, indium, titanium, or mixtures thereof; (3) sources of an oxide selected from oxides of silicon, germanium or mixtures thereof; and (4) at least one quaternary ammonium cation capable of forming the zeolite and having the following formula:

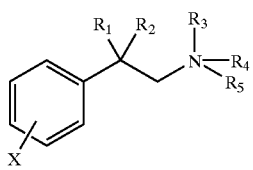

Formula (I)

wherein:
    X is —H, methyl, —F, —Cl, —F and —Cl, or methoxy;
    $R_1$ and $R_2$ are each methyl or ethyl; $R_1$ and $R_2$ together are —(CH$_2$)$_x$— where x is 2, 3, 4, or 5; or $R_1$ and $R_2$ together are methylated or dimethylated —(CH$_2$)$_y$— where y is 3, 4, or 5; and
    $R_3$, $R_4$ and $R_5$ are each methyl or ethyl, or one of $R_3$, $R_4$ or $R_5$ is methyl and the other two together are —(CH$_2$)$_z$— where z is 4, 5, 6 or 7;
    (b) maintaining the aqueous solution under conditions sufficient to form crystals of the zeolite; and
    (c) recovering the crystals of the zeolite.

2. The process of claim 1 wherein said aqueous solution comprises, in terms of mole ratios, the following:

YO$_2$/W$_a$O$_b$ 20–∞
OH$^-$/YO$_2$ 0.10–0.50
Q/YO$_2$ 0.05–0.50
M$_{2/n}$/YO$_2$ 0.02–0.40
H$_2$O/YO$_2$ 10–100 where Y is silicon, germanium or mixtures thereof; W is aluminum, boron, iron, gallium, indium, titanium, vanadium or mixtures thereof, a is 1 or 2, and b is 2 when a is 1 (i.e., W is tetravalent) and b is 3 when a is 2 (i.e., W is trivalent); Q is at least one quaternary ammonium cation capable of forming the zeolite and having formula (I); M is an alkali metal, alkaline earth metal or mixtures thereof; and n is the valence of M.

3. The process of claim 1 wherein the quaternary ammonium cation is selected from the group consisting of cations having the following structures:

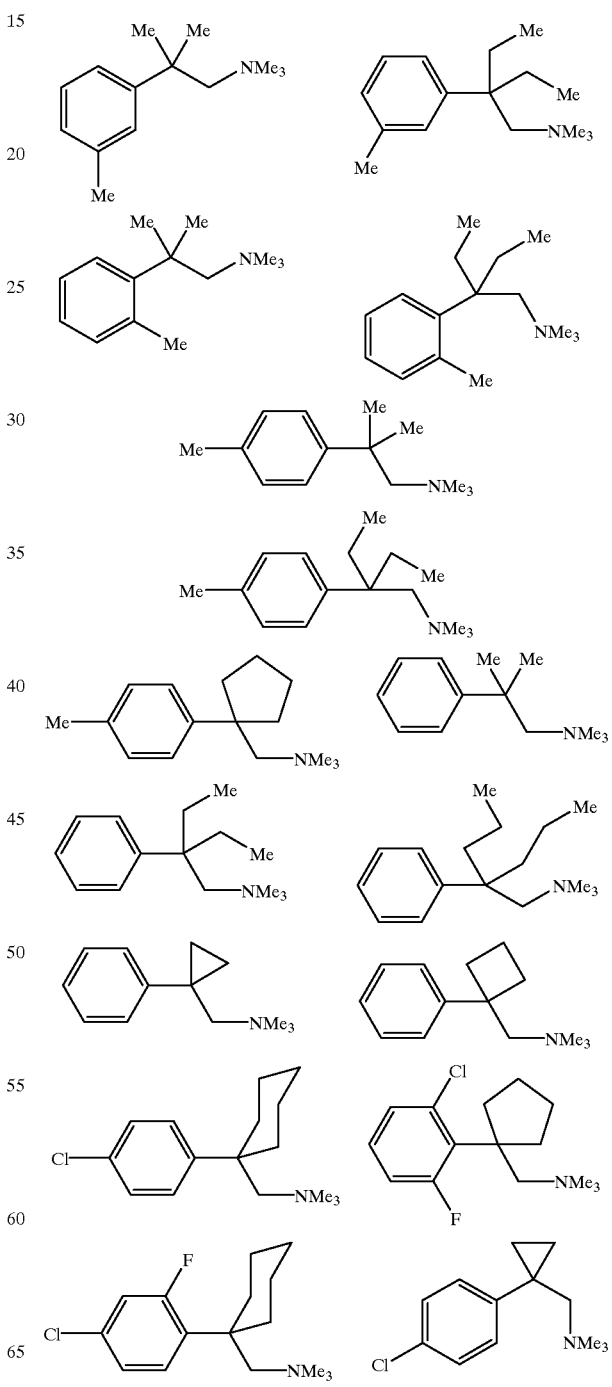

-continued

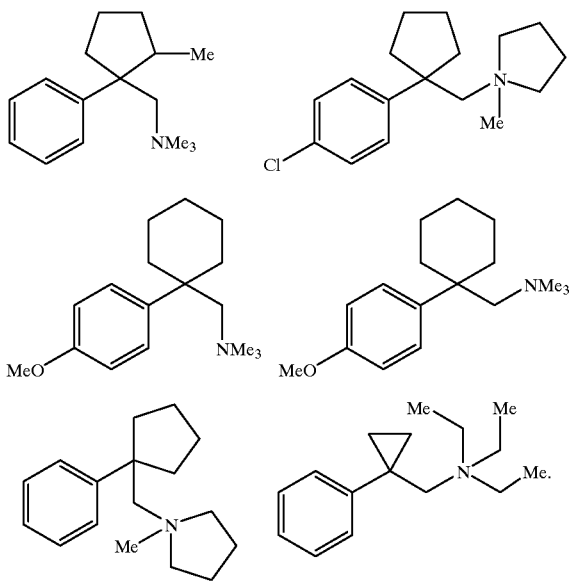

4. The process of claim 1 wherein the quaternary ammonium cation is

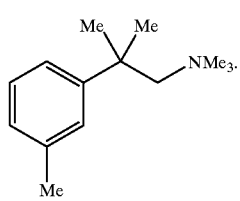

5. The process of claim 1 wherein the quaternary ammonium cation is

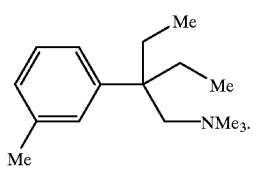

6. The process of claim 1 wherein the quaternary ammonium cation is

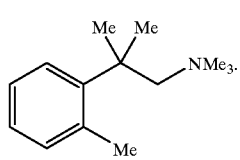

7. The process of claim 1 wherein the quaternary ammonium cation is

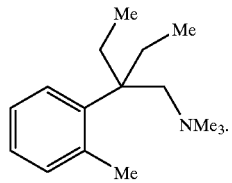

8. The process of claim 1 wherein the quaternary ammonium cation is

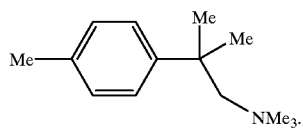

9. The process of claim 1 wherein the quaternary ammonium cation is

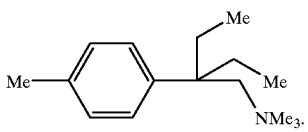

10. The process of claim 1 wherein the quaternary ammonium cation is

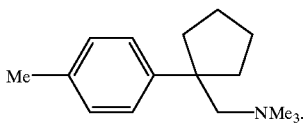

11. The process of claim 1 wherein the quaternary ammonium cation is

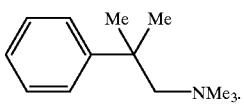

12. The process of claim 1 wherein the quaternary ammonium cation is

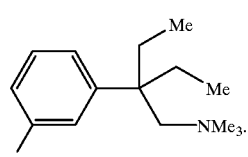

13. The process of claim 1 wherein the quaternary ammonium cation is

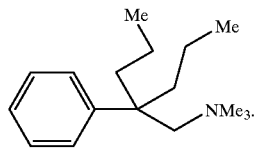

14. The process of claim 1 wherein the quaternary ammonium cation is

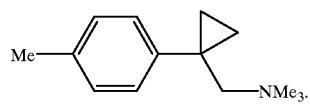

15. The process of claim 1 wherein the quaternary ammonium cation is

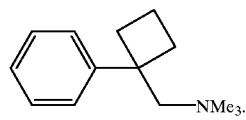

16. The process of claim 1 wherein the quaternary ammonium cation is

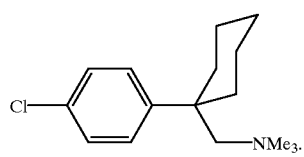

17. The process of claim 1 wherein the quaternary ammonium cation is

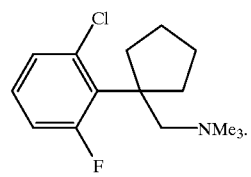

18. The process of claim 1 wherein the quaternary ammonium cation is

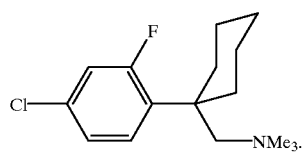

19. The process of claim 1 wherein the quaternary ammonium cation is

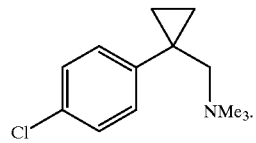

20. The process of claim 1 wherein the quaternary ammonium cation is

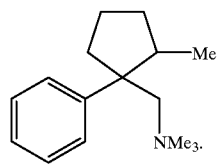

21. The process of claim 1 wherein the quaternary ammonium cation is

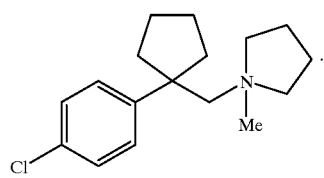

22. The process of claim 1 wherein the quaternary ammonium cation is

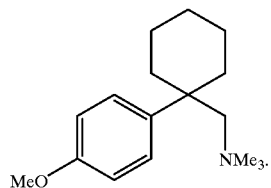

23. The process of claim 1 wherein the quaternary ammonium cation is

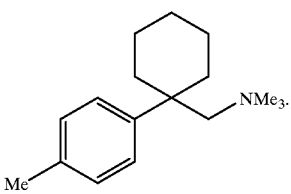

24. The process of claim 1 wherein the quaternary ammonium cation is

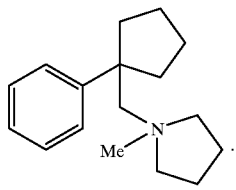

25. The process of claim 1 wherein the quaternary ammonium cation is

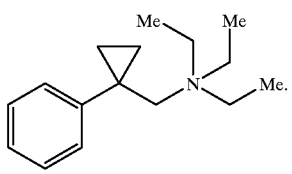

26. The process of claim 1 wherein the zeolite is ZSM-39 and the quaternary ammonium cation is

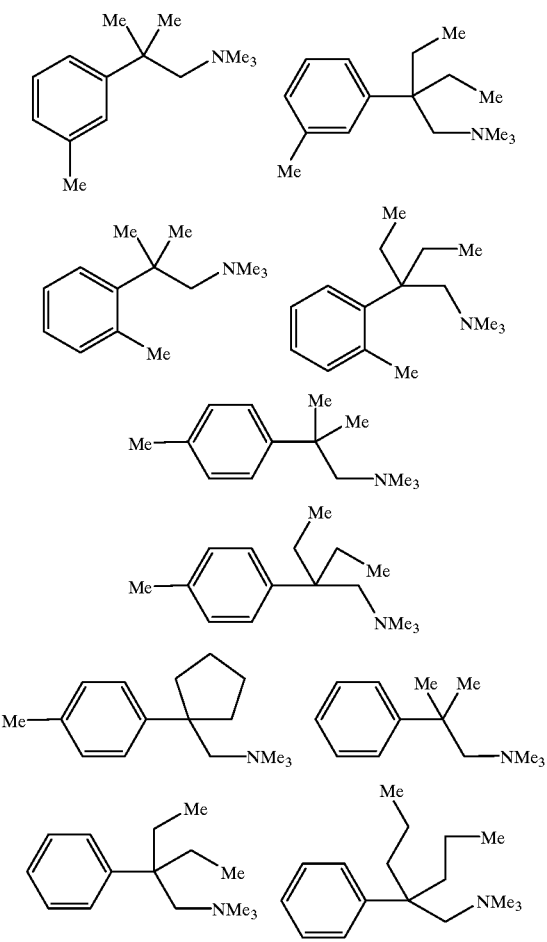

-continued

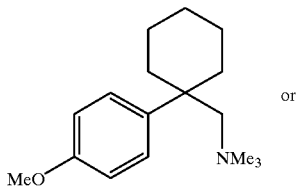

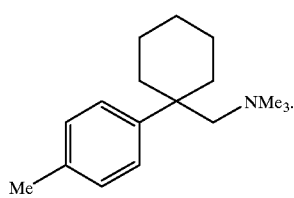

27. The process of claim 1 wherein the zeolite is ZSM-51 and the quaternary ammonium cation is

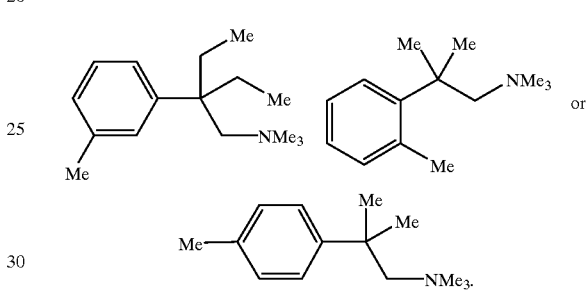

28. The process of claim 1 wherein the zeolite is ZSM-48 and the quaternary ammonium cation is

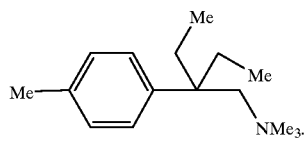

29. The process of claim 1 wherein the zeolite is ZSM-5 and the quaternary ammonium cation is

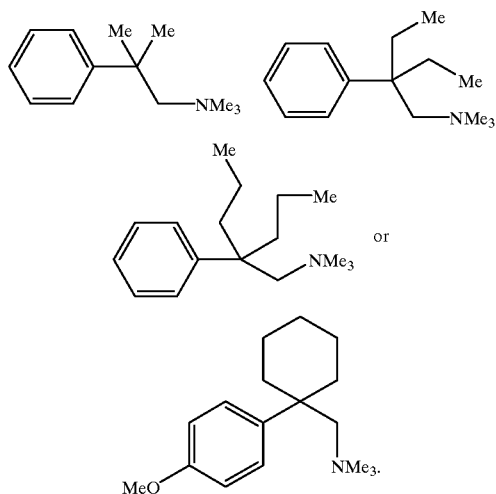

30. The process of claim 1 wherein the zeolite is ZSM-12 and the quaternary ammonium cation is

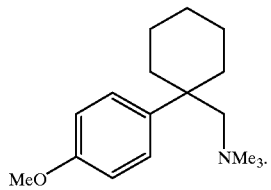

31. The process of claim 1 wherein the zeolite is SSZ-48 and the quaternary ammonium cation is

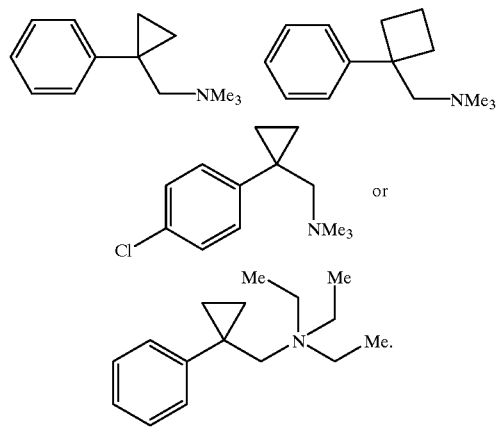

32. The process of claim 1 wherein the zeolite is SSZ-53 and the quaternary ammonium cation is

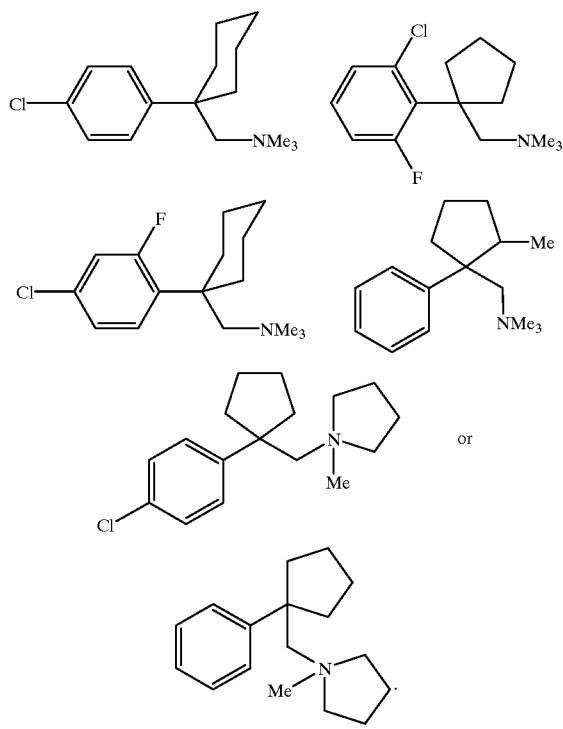

33. The process of claim 1 further comprising replacing the alkali metal cations, alkaline earth metal cations, or both of the recovered zeolite, at least in part, by ion exchange with a cation or mixture of cations selected from the group consisting of hydrogen and hydrogen precursors, rare earth metals, and metals from Groups IIA, IIIA, IVA, IB, IIB, IIIB, IVB, VIB, and VIII of the Periodic Table of Elements.

34. The process of claim 33 wherein said replacing cation is hydrogen or a hydrogen precursor.

35. A zeolite composition, as-synthesized and in the anhydrous state, whose general formula, in terms of mole ratios, is as follows:

$YO_2/W_cO_d \geqq 20$ $Q/YO_2$ 0.02–0.10

$M_{2/n}/YO_2$ 0.01–0.10 wherein Y is silicon, germanium or a mixture thereof; W is aluminum, boron, gallium, indium, iron, titanium, vanadium or mixtures thereof; c is 1 or 2; d is 2 when c is 1 (i.e., W is tetravalent) or d is 3 or 5 when c is 2 (i.e., d is 3 when W is trivalent or 5 when W is pentavalent); Q is at least one quaternary ammonium cation capable of forming the zeolite and having the formula

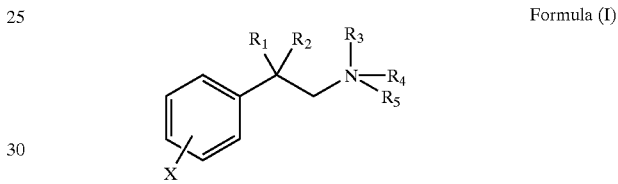

Formula (I)

wherein:

X is —H, methyl, —F, —Cl, —F and —Cl, or methoxy;

$R_1$ and $R_2$ are each methyl or ethyl; $R_1$ and $R_2$ together are —$(CH_2)_x$— where x is 2, 3, 4, or 5; or $R_1$ and $R_2$ together are methylated or dimethylated —$(CH_2)_y$— where y is 3, 4, or 5; and $R_3$, $R_4$ and $R_5$ are each methyl or ethyl, or one of $R_3$, $R_4$ or $R_5$ is methyl and the other two together are —$(CH_2)_z$— where z is 4, 5, 6 or 7.

36. The composition of claim 35 wherein Q is selected from the group consisting of cations having the following structures:

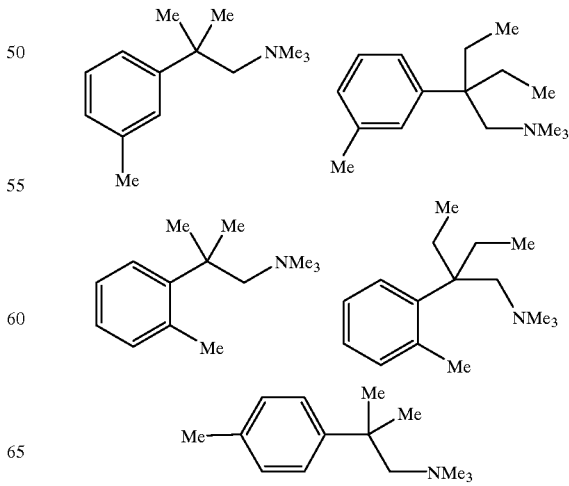

-continued
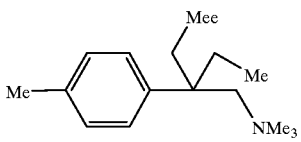
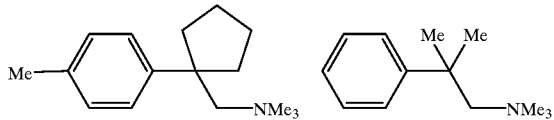
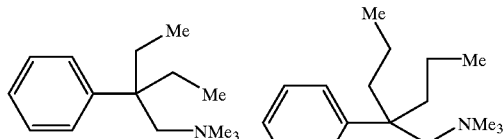
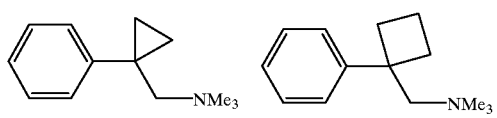
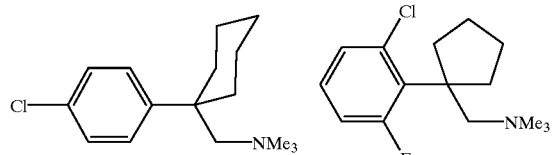
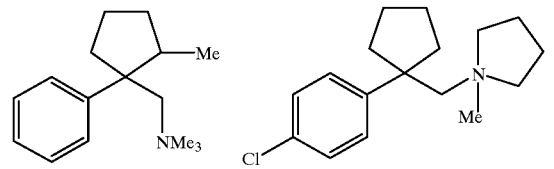
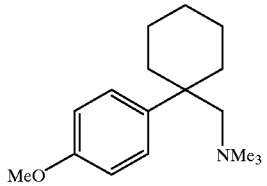
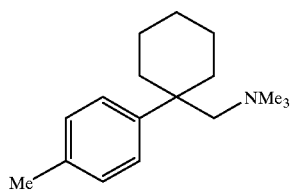
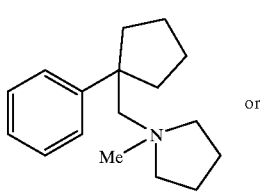 or
-continued
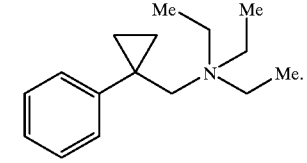
37. The composition of claim 35 wherein Q is
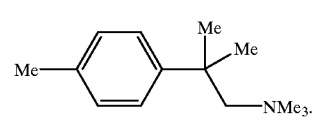
38. The composition of claim 35 wherein Q is
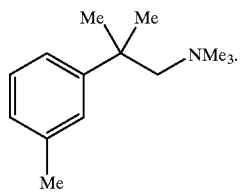
39. The composition of claim 35 wherein Q is
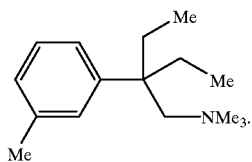
40. The composition of claim 35 wherein Q is
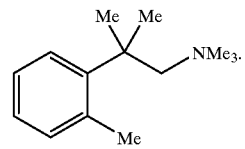
41. The composition of claim 35 wherein Q is
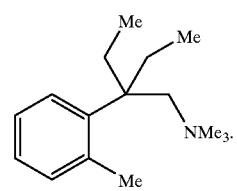
42. The composition of claim 35 wherein Q is
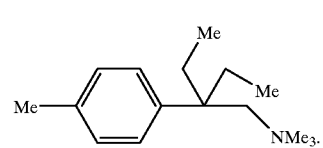

43. The composition of claim 35 wherein Q is

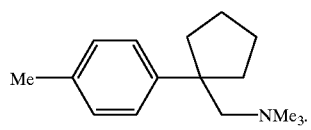

44. The composition of claim 35 wherein Q is

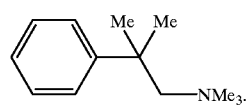

45. The composition of claim 35 wherein Q is

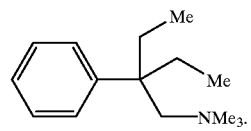

46. The composition of claim 35 wherein Q is

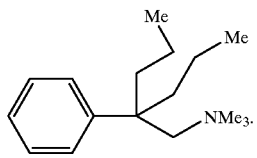

47. The composition of claim 35 wherein Q is

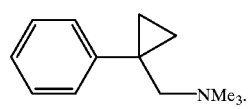

48. The composition of claim 35 wherein Q is

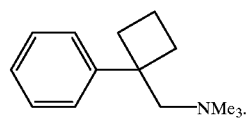

49. The composition of claim 35 wherein Q is

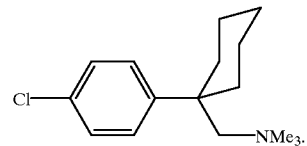

50. The composition of claim 35 wherein Q is

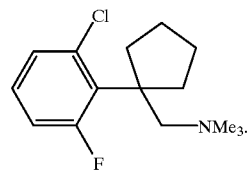

51. The composition of claim 35 wherein Q is

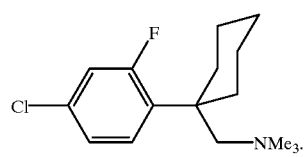

52. The composition of claim 35 wherein Q is

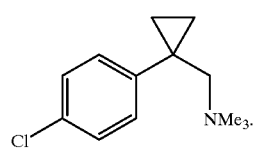

53. The composition of claim 35 wherein Q is

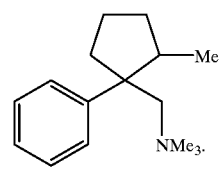

54. The composition of claim 35 wherein Q is

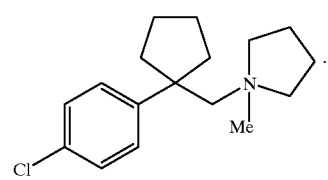

55. The composition of claim 35 wherein Q is

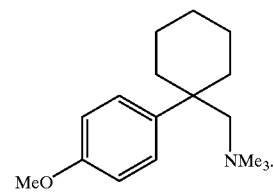

56. The composition of claim 35 wherein Q is
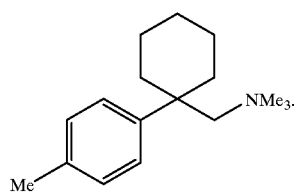
57. The composition of claim 35 wherein Q is
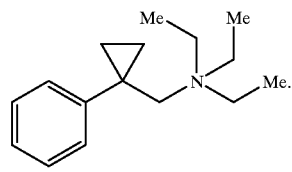
58. The composition of claim 35 wherein Q is
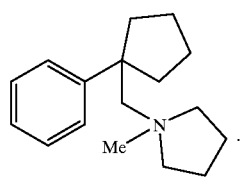
59. The composition of claim 35 wherein the zeolite is ZSM-39 and Q is
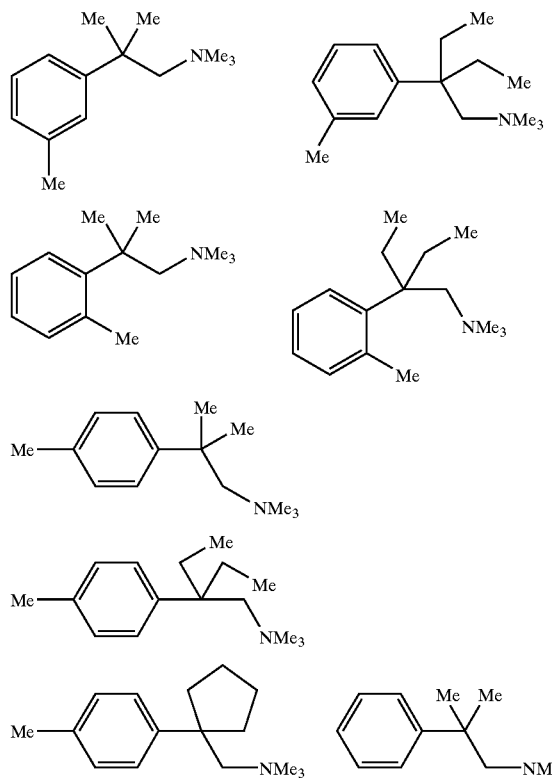
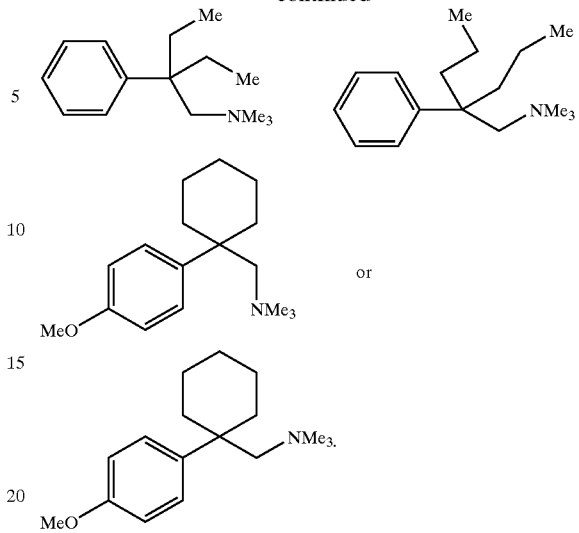
60. The composition of claim 35 wherein the zeolite is ZSM-51 and Q is
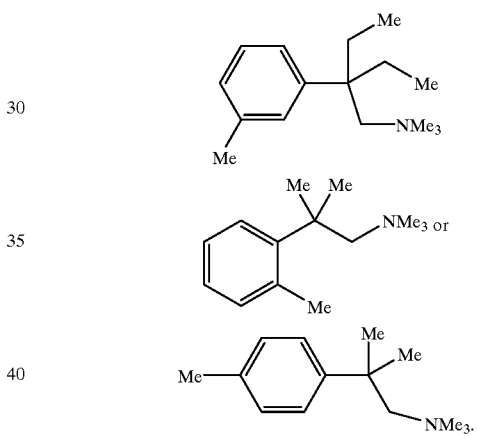
61. The composition of claim 35 wherein the zeolite is ZSM-48 and Q is
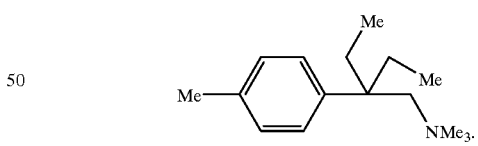
62. The composition of claim 35 wherein the zeolite is ZSM-5 and Q is
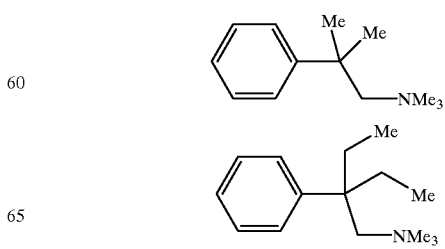

-continued
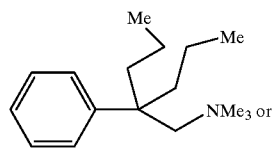
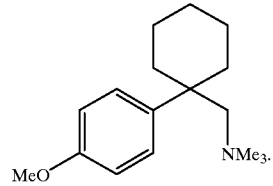
63. The composition of claim 35 wherein the zeolite is ZSM-12 and Q is
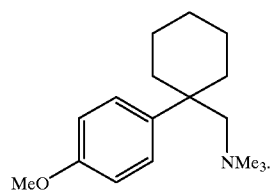
64. The composition of claim 35 wherein the zeolite is SSZ-48 and Q is
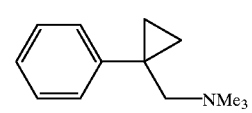 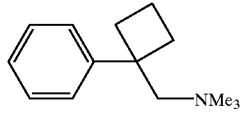
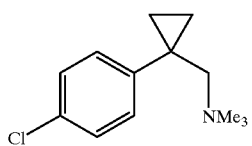 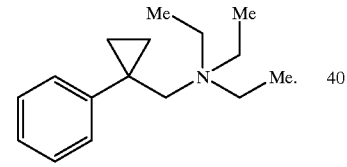
65. The composition of claim 35 wherein the zeolite is SSZ-53 and Q is
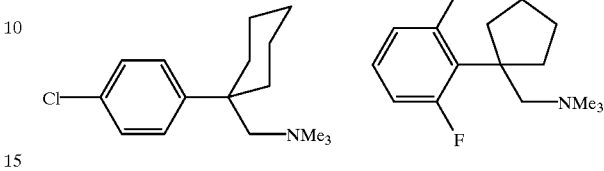 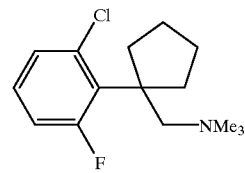
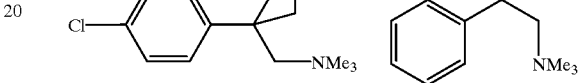 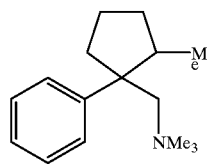
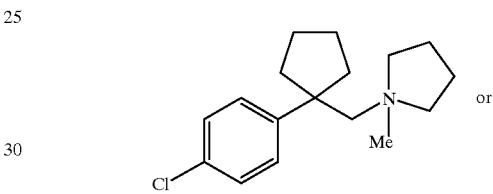 or
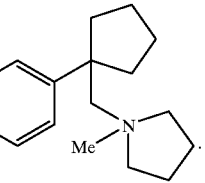
* * * * *